US012291501B2

(12) United States Patent
Horenstein et al.

(10) Patent No.: US 12,291,501 B2
(45) Date of Patent: *May 6, 2025

(54) N,N DIETHYL-N'PHENYLPIPERAZINE ALPHA 7 AND ALPHA 9 NICOTINIC ACETYLCHOLINE RECEPTOR AGONISTS AND ANTAGONISTS

(71) Applicant: University of Florida Research Foundation, Inc., Gainesville, FL (US)

(72) Inventors: Nicole Alana Horenstein, High Springs, FL (US); Roger Lee Papke, Gainesville, FL (US); Hina Andleeb, Boston, MA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,322

(22) Filed: Nov. 30, 2023

(65) Prior Publication Data

US 2024/0092738 A1 Mar. 21, 2024

Related U.S. Application Data

(63) Continuation of application No. 17/903,735, filed on Sep. 6, 2022, now Pat. No. 11,884,629.

(60) Provisional application No. 63/241,611, filed on Sep. 8, 2021.

(51) Int. Cl.
*C07D 213/56* (2006.01)
*C07D 263/32* (2006.01)
*C07D 295/116* (2006.01)

(52) U.S. Cl.
CPC ......... *C07D 213/56* (2013.01); *C07D 263/32* (2013.01); *C07D 295/116* (2013.01)

(58) Field of Classification Search
CPC . C07D 213/56; C07D 263/32; C07D 295/116
See application file for complete search history.

(56) References Cited

U.S. PATENT DOCUMENTS

| | | | | |
|---|---|---|---|---|
| 10,662,191 | B2 * | 5/2020 | Horenstein | C07D 295/096 |
| 11,155,551 | B2 * | 10/2021 | Horenstein | A61K 31/452 |
| 11,299,496 | B2 * | 4/2022 | Thakur | A61P 25/18 |
| 11,884,629 | B2 * | 1/2024 | Horenstein | C07D 295/116 |
| 2009/0325929 | A1 * | 12/2009 | Li | C07D 513/10 |
| | | | | 544/231 |
| 2018/0298002 | A1 * | 10/2018 | Horenstein | C07D 211/58 |
| 2020/0369674 | A1 * | 11/2020 | Li | A61P 25/04 |
| 2021/0332046 | A1 * | 10/2021 | Horenstein | A61K 31/42 |

FOREIGN PATENT DOCUMENTS

| | | | | |
|---|---|---|---|---|
| CN | 101440073 B | * | 2/2011 | |
| WO | WO-2023278986 A1 | * | 1/2023 | ........... A61K 31/495 |

OTHER PUBLICATIONS

Gao; Inflamm. Res. 2018, 67, 363-370. https://doi.org/10.1007/s00011-017-1127-2 (Year: 2018).*
Li; Inflammation 2020, 43, 903-915. https://doi.org/10.1007/s10753-020-01177-1 (Year: 2020).*
Quadri; Journal of Pharmacology and Experimental Therapeutics 2018, 367, 203-214. https://doi.org/10.1124/jpet.118.249904 (Year: 2018).*
Quadri; Bioorg. Med. Chem. 2016, 24, 286-293. http://dx.doi.org/10.1016/j.bmc.2015.12.017 (Year: 2016).*
Wang; Neurochem Res 2019, 44, 2786-2795. https://doi.org/10.1007/s11064-019-02899-x (Year: 2019).*
Hogg, R C et al. "Nicotinic acetylcholine receptors: from structure to brain function." Reviews of physiology, biochemistry and pharmacology vol. 147 (2003): 1-46. doi: 10.1007/s10254-003-0005-1(abstract only).
Halder, Namrita, and Girdhari Lal. "Cholinergic System and Its Therapeutic Importance in Inflammation and Autoimmunity." Frontiers in immunology vol. 12 660342. Apr. 15, 2021, doi: 10.3389/fimmu.2021.660342.
Dani, John A, and Daniel Bertrand. "Nicotinic acetylcholine receptors and nicotinic cholinergic mechanisms of the central nervous system." Annual review of pharmacology and toxicology vol. 47 (2007): 699-729. doi: 10.1146/annurev.pharmtox.47.120505.105214.
Millar, Neil S, and Cecilia Gotti. "Diversity of vertebrate nicotinic acetylcholine receptors." Neuropharmacology vol. 56,1 (2009): 237-46. doi:10.1016/j.neuropharm.2008.07.041.
Elgoyhen et al., "α9: An Acetylcholine Receptor with Novel Pharmacological in Rat Cochlear Hair Cells" (1994) Cell 79: 705-715).
Gotti, Cecilia et al. "Selective nicotinic acetylcholine receptor subunit deficits identified in Alzheimer's disease, Parkinson's disease and dementia with Lewy bodies by immunoprecipitation." Neurobiology of disease vol. 23,2 (2006): 481-9. doi:10.1016/j.nbd.2006.04.005.
Takeuchi, Hiroki et al. "Nicotinic receptor stimulation protects nigral dopaminergic neurons in rotenone-induced Parkinson's disease models." Journal of neuroscience research vol. 87,2 (2009): 576-85. doi: 10.1002/jnr.21869.

(Continued)

*Primary Examiner* — Daniel R Carcanague
(74) *Attorney, Agent, or Firm* — Thomas | Horstemeyer LLP

(57) ABSTRACT

Provided are embodiments of para-substituted 1,1-dialkyl-4-phenylpiperazin-1-ium iodides advantageous for modulating inflammation that have been synthesized and their electrophysiology activities for α9, α9α10, and α7 nAChRs compared. The para position contained alkyl or aryl amides, or heterocyclic isosteres for the amide, and the alkyl groups were varied at the ammonium piperazine nitrogen to see if compensatory changes in size at this position of the molecule impacted function. The compounds were characterized with two-electrode voltage-clamp measurements on Xenopus oocytes expressing nAChRs. General, the compounds were more potent for α9-containing receptors than for α7, and the majority were either full or strong partial agonists for α9-containing nAChR.

14 Claims, 12 Drawing Sheets

(56) References Cited

OTHER PUBLICATIONS

Mohammadi, Sarasa A, and MacDonald J Christie. "Conotoxin Interactions with α9α10-nAChRs: Is the α9α10-Nicotinic Acetylcholine Receptor an Important Therapeutic Target for Pain Management?." Toxins vol. 7,10 3916-32. Sep. 28, 2015, doi:10.3390/toxins7103916.
Gu, Shenyan et al. "Hair cell α9α10 nicotinic acetylcholine receptor functional expression regulated by ligand binding and deafness gene products." Proceedings of the National Academy of Sciences of the United States of America vol. 117,39 (2020): 24534-24544. doi:10.1073/pnas.2013762117.
Piovesana et al., Cholinergic Modulation of Neuroinflammation: Focus on α7, Nicotinic Receptor, Int. J. Mol. Sci. 2021, 22, 4912. https://doi.org/10.3390/ijms22094912.
Papke, Roger L, and Jon M Lindstrom. "Nicotinic acetylcholine receptors: Conventional and unconventional ligands and signaling." Neuropharmacology vol. 168 (2020): 108021. doi: 10.1016/j.neuropharm.2020.108021.
Bagdas, Deniz et al. "New Insights on Neuronal Nicotinic Acetylcholine Receptors as Targets for Pain and Inflammation: A Focus on α7 nAChRs." Current neuropharmacology vol. 16,4 (2018): 415-425. doi: 10.2174/1570159X15666170818102108.
Toma, Wisam et al. "Behavioral and Molecular Basis of Cholinergic Modulation of Pain: Focus on Nicotinic Acetylcholine Receptors." Current topics in behavioral neurosciences vol. 45 (2020): 153-166. doi: 10.1007/7854_2020_135.
Hone, Arik J et al. "α9-containing nicotinic acetylcholine receptors and the modulation of pain." British journal of pharmacology vol. 175,11 (2018): 1915-1927. doi:10.1111/bph.13931.
Romero, Haylie K et al. "Inhibition of α9α10 nicotinic acetylcholine receptors prevents chemotherapy-induced neuropathic pain." Proceedings of the National Academy of Sciences of the United States of America vol. 114,10 (2017): E1825-E1832. doi:10.1073/pnas.1621433114.
Elgoyhen, Ana Belén, and Eleonora Katz. "The efferent medial olivocochlear-hair cell synapse." Journal of physiology, Paris vol. 106, 1-2 (2012): 47-56. doi:10.1016/j.jphysparis.2011.06.001.
Plazas, Paola V et al. "Stoichiometry of the alpha9alpha10 nicotinic cholinergic receptor." The Journal of neuroscience : the official journal of the Society for Neuroscience vol. 25,47 (2005): 10905-12. doi: 10.1523/JNEUROSCI.3805-05.2005.
Elgoyhen, A B et al. "alpha10: a determinant of nicotinic cholinergic receptor function in mammalian vestibular and cochlear mechanosensory hair cells." Proceedings of the National Academy of Sciences of the United States of America vol. 98,6 (2001): 3501-6. doi:10.1073/pnas.051622798.
Marcela Lipovsek, et al., "Tracking the Molecular Evolution of Calcium Permeability in a Nicotinic Acetylcholine Receptor", Mol. Biol. Evol. 31(12):3250-3265 doi: 10.1093/molbev/msu258 (2014).
Callaghan, Brid, and David J Adams. "Analgesic α-conotoxins Vc1.1 and RgIA inhibit N-type calcium channels in sensory neurons of α9 nicotinic receptor knockout mice." Channels (Austin, Tex.) vol. 4,1 (2010): 51-4. doi: 10.4161/chan.4.1.10281.
Lips et al., "Coexpression of K9 and K10 Nicotinic Acetylcholine Receptors in Rat Dorsal Root Ganglion Neurons", Neuroscience vol. 115, No. 1, pp. 1-5, 2002.
Ellison, Michael et al. "Alpha-RgIA: a novel conotoxin that specifically and potently blocks the alpha9alpha10 nAChR." Biochemistry vol. 45,5 (2006): 1511-7. doi:10.1021/bi0520129.
Biallas, Simone et al. "Immunohistochemical detection of nicotinic acetylcholine receptor subunits alpha9 and alpha10 in rat lung isografts and allografts." Life sciences vol. 80,24-25 (2007): 2286-9. doi:10.1016/j.lfs.2007.01.043.
Elgoyhen, Ana Belén et al. "The nicotinic receptor of cochlear hair cells: a possible pharmacotherapeutic target?." Biochemical pharmacology vol. 78,7 (2009): 712-9. doi: 10.1016/j.bcp.2009.05.023.
Papke, Roger L et al. "Selective Agonists and Antagonists of α9 Versus α7 Nicotinic Acetylcholine Receptors." ACS chemical neuroscience vol. 13,5 (2022): 624-637. doi: 10.1021/acschemneuro.1c00747.
Richter, Katrin et al. "Comparison of the Anti-inflammatory Properties of Two Nicotinic Acetylcholine Receptor Ligands, Phosphocholine and pCF3-diEPP." Frontiers in cellular neuroscience vol. 16 779081. Mar. 31, 2022, doi: 10.3389/fncel.2022.779081.

* cited by examiner

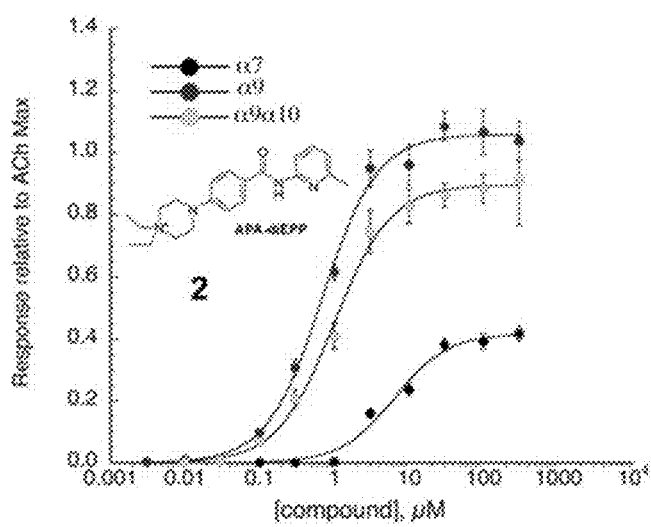
Fig. 6A
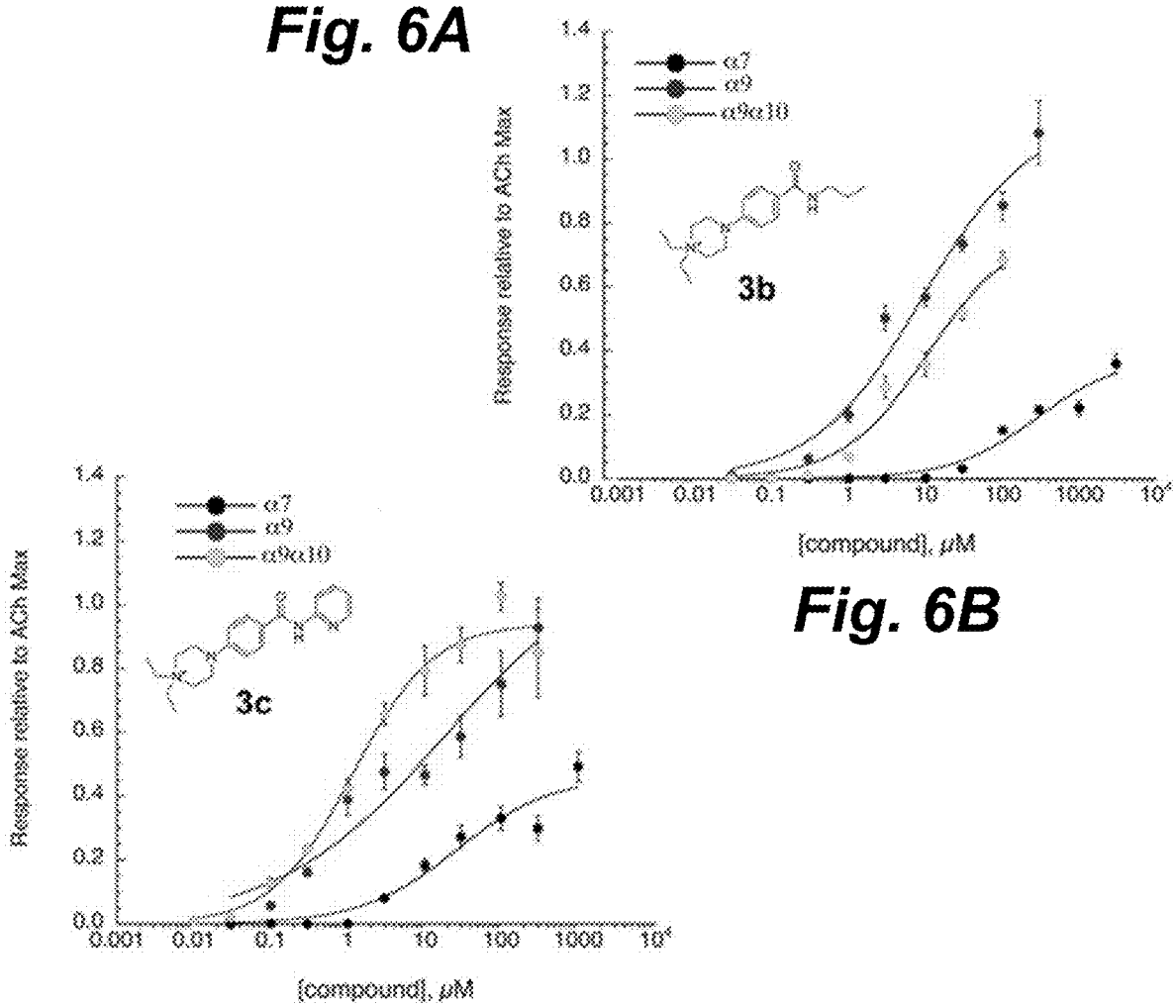
Fig. 6B
Fig. 6C

Scheme for the synthesis of APA-diEPP. Reagents: (a) LiHMDS [1.0M in THF] (3.0 equiv); (b) N-ethylpiperazine, tris(dibenzylideneacetone)dipalladium(0) (10 mol%), cesium carbonate (2.0 equiv), BINAP (30 mol%), dioxane; (c) iodoethane, THF

N,N DIETHYL-N'PHENYLPIPERAZINE ALPHA 7 AND ALPHA 9 NICOTINIC ACETYLCHOLINE RECEPTOR AGONISTS AND ANTAGONISTS

CROSS-REFERENCE TO RELATED APPLICATIONS

This application is a continuation of U.S. Nonprovisional patent application Ser. No. 17/903,735 filed on Sep. 6, 2022, which claims priority to U.S. Provisional Patent Application Ser. No. 63/241,611 entitled "N,N DIETHYL-N'PHENYLPIPERAZINE ALPHA 7 AND ALPHA 9 NICOTINIC ACETYLCHOLINE RECEPTOR AGONISTS AND ANTAGONISTS" filed Sep. 8, 2021, the entirety of which is hereby incorporated by reference.

STATEMENT REGARDING FEDERALLY SPONSORED RESEARCH OR DEVELOPMENT

This invention was made with Government support under contract R01 GM057481 awarded by the National Institutes of Health. The Government has certain rights in the invention.

TECHNICAL FIELD

The present disclosure is generally related to agonists and antagonists of α7 and α9 nicotinic acetylcholine receptors.

BACKGROUND

Nicotinic acetylcholine receptors (nAChRs) are cation-selective, ligand-gated ion channels that mediate a diverse range of physiologic processes, including fast neurotransmission in the peripheral nervous systems (at the skeletal neuromuscular junction and in the autonomic nervous system), modulation of synaptic function in the central nervous system, and immunomodulatory functions (Hogg et al., (2003) *Rev. Physiol. Biochem. Pharmacol.* 147: 1-46; Halder & Lal (2021) *Front. Immunol.* 12: 660342) in peripheral tissues.

Functional nAChR assemblies of five identical or different subunits, giving rise to homomeric or heteromeric pentamers, respectively (Dani & Bertrand (2007) *Annu. Rev. Pharmacol. Toxicol.* 47: 699-729). Neuronal nAChRs are formed from amongst nine identified α (α2 to α10) and three β (β2 to β4) subunits (Millar & Gotti (2009) *Neuropharmacol.* 56: 237-246). With the exception of α9 homomeric and α9α10 heteromeric receptors (Elgoyhen et al., (1994) *Cell* 79: 705-715), all known nAChRs respond to nicotine, thus naming the subfamily.

It has been proposed that nAChRs can be modulated to treat various nervous-system disorders, such as Alzheimer's disease, schizophrenia, depression, attention deficit hyperactivity disorder (ADHD), and tobacco addiction (Gotti et al., (2006) *Neurobiol. Dis.* 23: 481-489; Takeuchi et al., (2009) *J. Neurosci. Res.* 87(2): 576-585), as well as chronic pain (Mohammadi & Christie (2015) *Toxins (Basel)* 7: 3916-3932), Parkinson's disease (Quik et al., Gu et al., (2020) *Proc. Natl. Acad. Sci. U.S.A* 117: 24534-24544). Functional expression of nAChRs now enables drug discovery for these unmet medical needs.

Much of the work regarding nAChRs as therapeutic targets has focused on the subtypes expressed at high levels in the brain, i.e. heteromeric receptors containing α4 and β2 subunits and homomeric α7-containing receptors. However, the identification of nAChR expression in a variety of immune cells has provided evidence for a cholinergic anti-inflammatory pathway (CAP) (Piovesana et al., (2021) *Int. J. Mol. Sci.* 22; Reale & Costantini (2021) *Diseases* 9) that modulates inflammatory disease and neuropathic pain. This discovery has promoted a new direction for the development of therapeutics.

The function of nAChRs in the CAP may rely more on metabotropic than ionotropic signaling (Papke & Lindstrom (2020) *Neuropharmacol.* 168: 108021; Bagdas et al., (2018) *Curr. Neuropharmacol.* 16: 415-425; Toma et al., (2020) *Curr. Top Behav. Neurosci.* 45: 153-166), and the receptors most strongly implicated as targets are α7 and the less-well-understood α9 and α9α10 receptors (Hone et al., (2018) *Br. J. Pharmacol.* 175(11): 1915-1927; Romero et al., (2017) *Proc. Natl. Acad. Sci. U.S.A* 114: E1825-E1832), which had only been associated with auditory function (Elgoyhen & Katz (2012) *J. Physiol. Paris* 106: 47-56; Elgoyhen et al., (2009) *Biochem. Pharmacol.* 78: 712-719). The α9 subunits are known to combine with α10 subunits to form α9α10 nAChRs with kinetic properties slightly different from homomeric α9 nAChRs, with a likely $(\alpha 9)_2(\alpha 10)_3$ stoichiometry (Plazas et al., (2005) *J. Neurosci.* 25: 10905-10912).

The heteromeric nAChRs on hair cells contain α9 and α10 subunits and have several distinguishing characteristics (Elgoyhen et al., (2001) *Proc. Natl. Acad. Sci. U.S.A* 98: 3501-3506). The α9α10 receptor features antagonism by nicotine, which typically agonizes nAChRs, and potent block by strychnine and bicuculline, which are also antagonists of glycine and GABA receptors, respectively (Elgoyhen et al., (2001) *Proc. Natl. Acad. Sci. U.S.A* 98: 3501-3506).

The α9α10 nAChRs are among the most calcium-permeable ligand-gated channels known (Lipovsek et al., (2014) *Mol. Biol. Evol.* 31: 3250-3265), although their endogenous ion channel activity has only been recorded in cochlear and vestibular hair cells. Expression of α9α10 has been described in dorsal root ganglion neurons (Callaghan & Adams (2010) *Channels (Austin)* 4: 51-54; Lips et al., (2002) *Neuroscience* 115: 1-5), lymphocytes, skin keratinocytes, the pars tuberalis of the pituitary (Ellison et al., (2006) *Biochemistry* 45(5): 1511-1517), alveolar macrophages, and in the lung parenchyma of native and transplanted lungs (Biallas et al., (2007) *Life Sci.* 80: 2286-2289).

The α9 and α10 subunits share homology with other nAChRs, yet are structurally and pharmacologically distinct, having the lowest degree of sequence similarity with other nAChRs, making them a promising target for the development of selective drugs. In addition to potentially modulating CAP, compounds that target α9 and α9α10 could be useful for treating a variety of hearing disorders such as noise-induced hearing loss or the debilitating disorders, vertigo, or tinnitus (Elgoyhen et al., (2009) *Biochem. Pharmacol.* 78: 712-719).

It has now been shown that compounds previously identified as silent agonists of α7, with potential metabotropic activity, could, based on specific structural epitopes, function as potent α9 agonists or antagonists (Papke et al., (2022) *ACS Chem. Neurosci.* 13: 624-637). It was confirmed that one of the α9 agonists was an effective modulator of inflammatory signaling in a cell-based assay (Richter et al., (2022) *Front. Cell Neurosci.* 16: 779081).

SUMMARY

One aspect of the disclosure encompasses embodiments of a para-substituted 1,1-dialkyl-4-phenylpiperazin-1-ium having the formula:

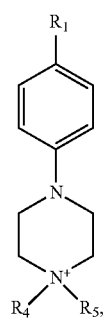

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the para-substituted 1,1-dialkyl-4-phenylpiperazin-1-ium is selected from the group consisting of the formulae:

3a
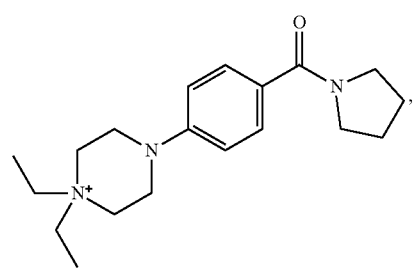

3b
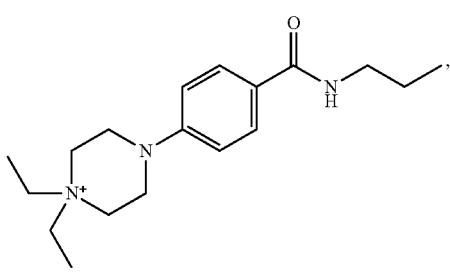

3c
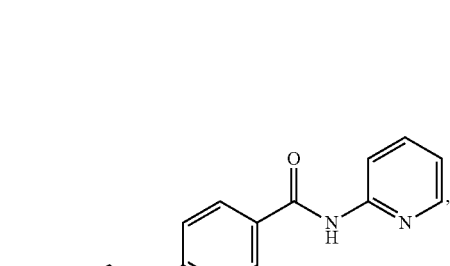

3d
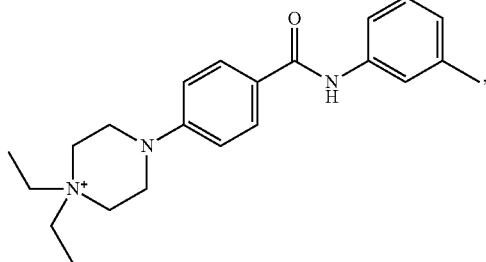

3e
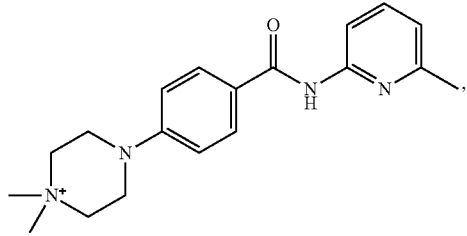

3f
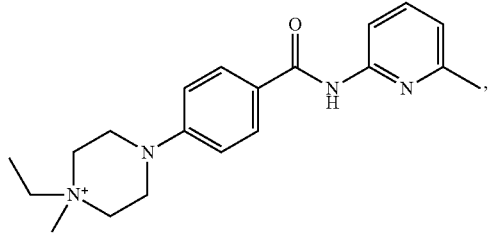

3g
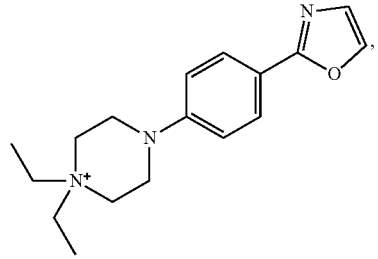

3h
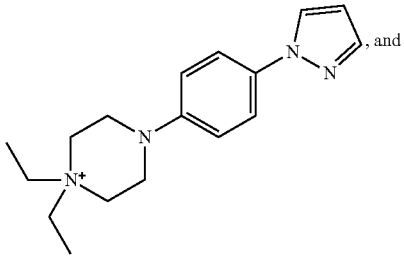
, and

3i
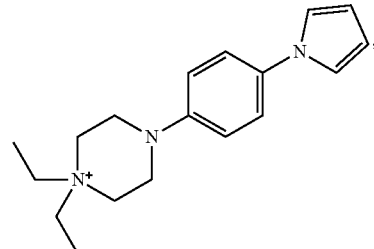

-continued

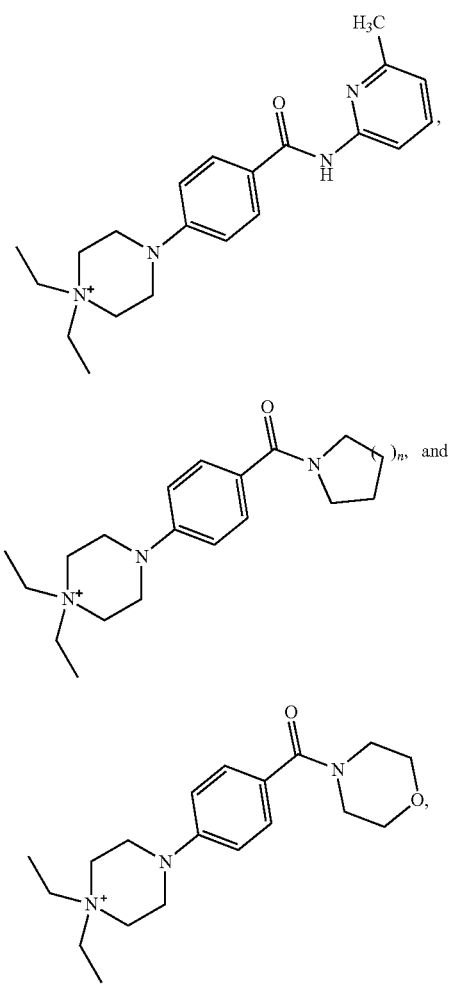

or a salt thereof.

In some embodiments of this aspect of the disclosure, the salt of the para-substituted 1,1-dialkyl-4-phenylpiperazin-1-ium can be an iodide.

Another aspect of the disclosure encompasses embodiments of a method of modulating the electrophysiological activity of a nicotinic acetylcholine receptor (nAChR) of an animal cell, the method comprising contacting an animal cell with a para-substituted 1,1-dialkyl-4-phenylpiperazin-1-ium having the formula:

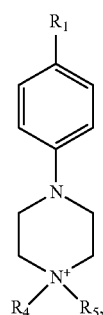

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the compound can be selected from the group consisting of the formulae:

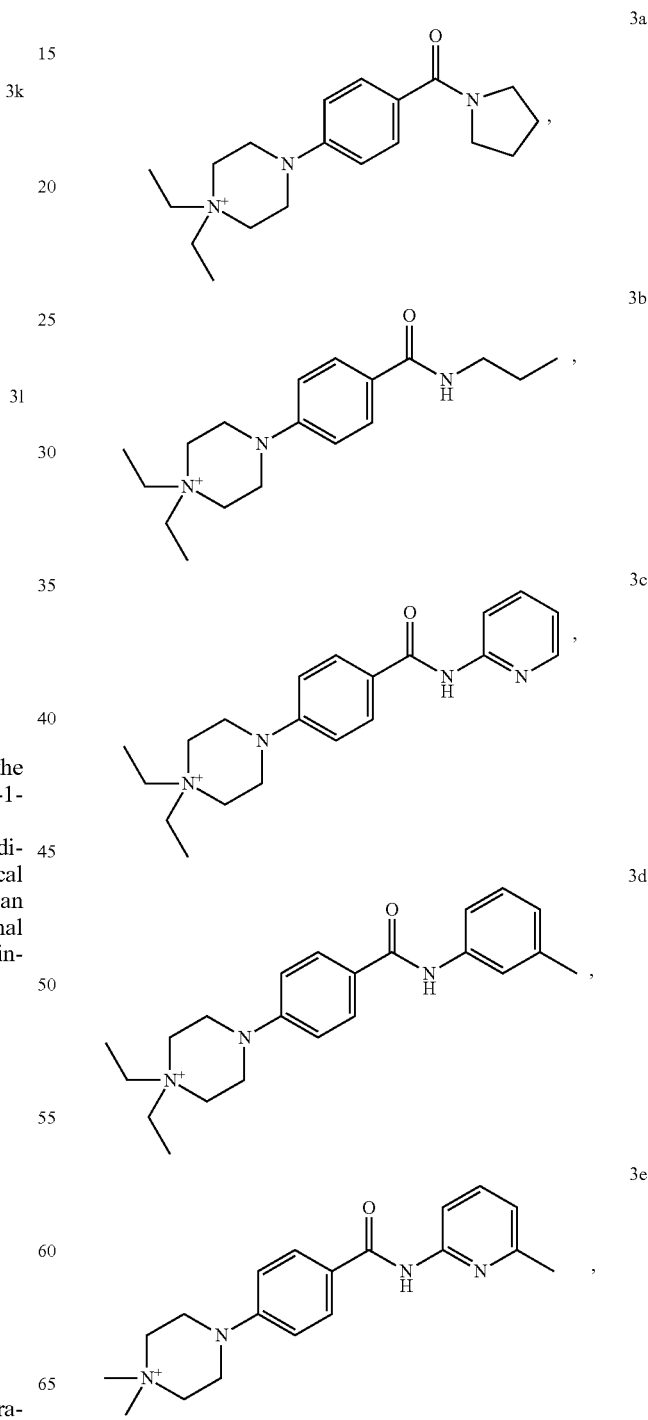

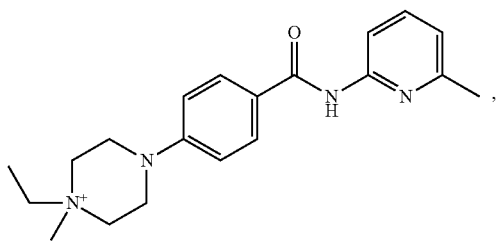

3f

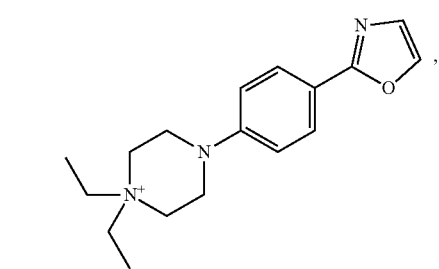

3g

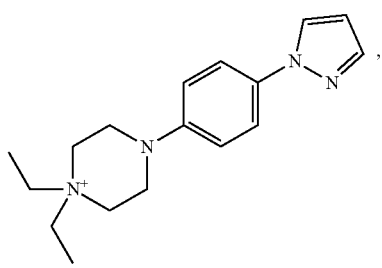

3h

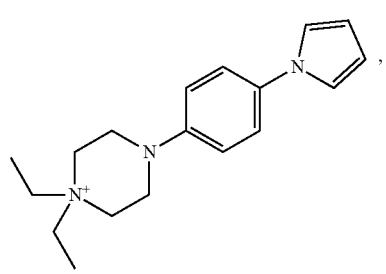

3i

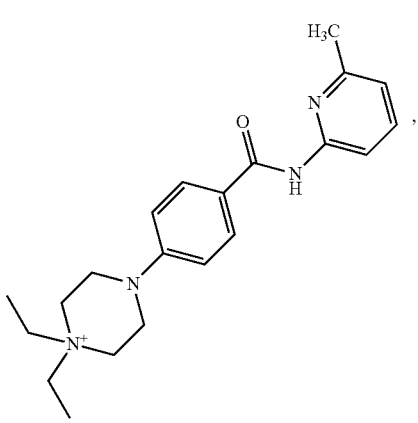

3j

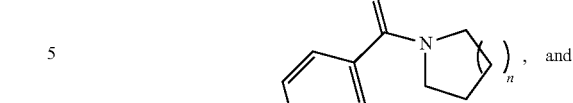

3k

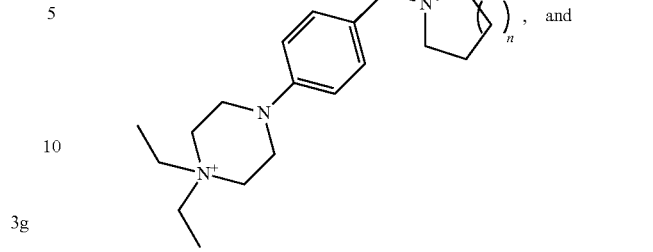

3l

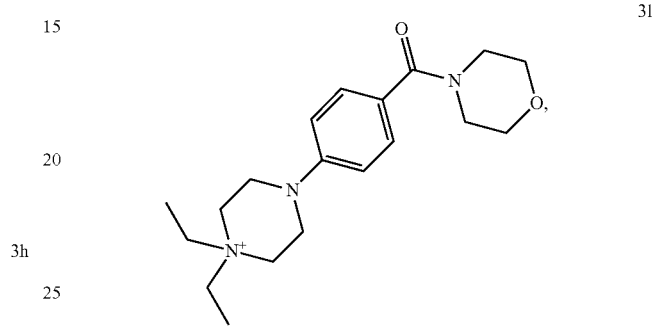

or a salt thereof.

In some embodiments of this aspect of the disclosure, the salt of the para-substituted 1,1-dialkyl-4-phenylpiperazin-1-ium can be an iodide.

In some embodiments of this aspect of the disclosure, the nAChR is an α9, an α9α10, or an α7 nAChR.

Yet another aspect of the disclosure encompasses embodiments of a method of modulating inflammatory signaling by modulating the electrophysiological activity of a nicotinic acetylcholine receptor (nAChR) of an animal cell, the method comprising delivering to an animal cell a para-substituted 1,1-dialkyl-4-phenylpiperazin-1-ium having the formula:

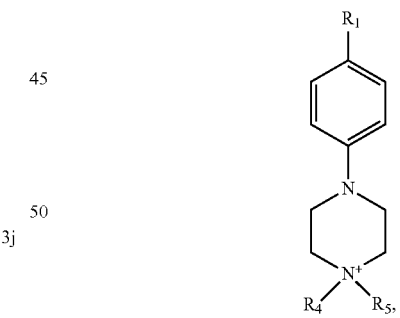

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the compound can be selected from the group consisting of the formulae:

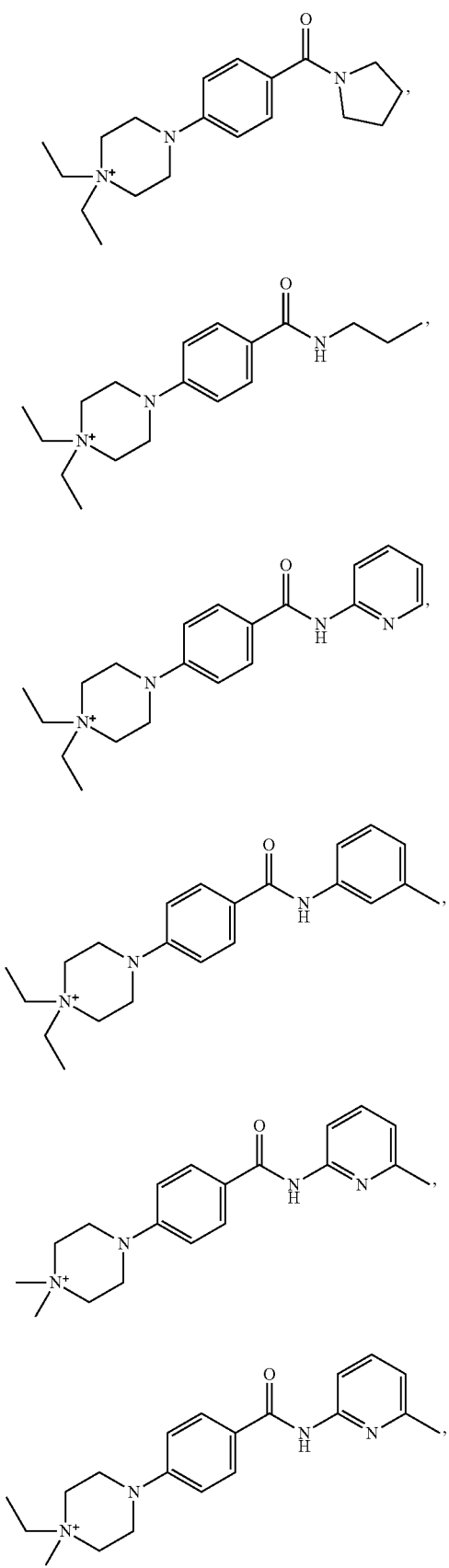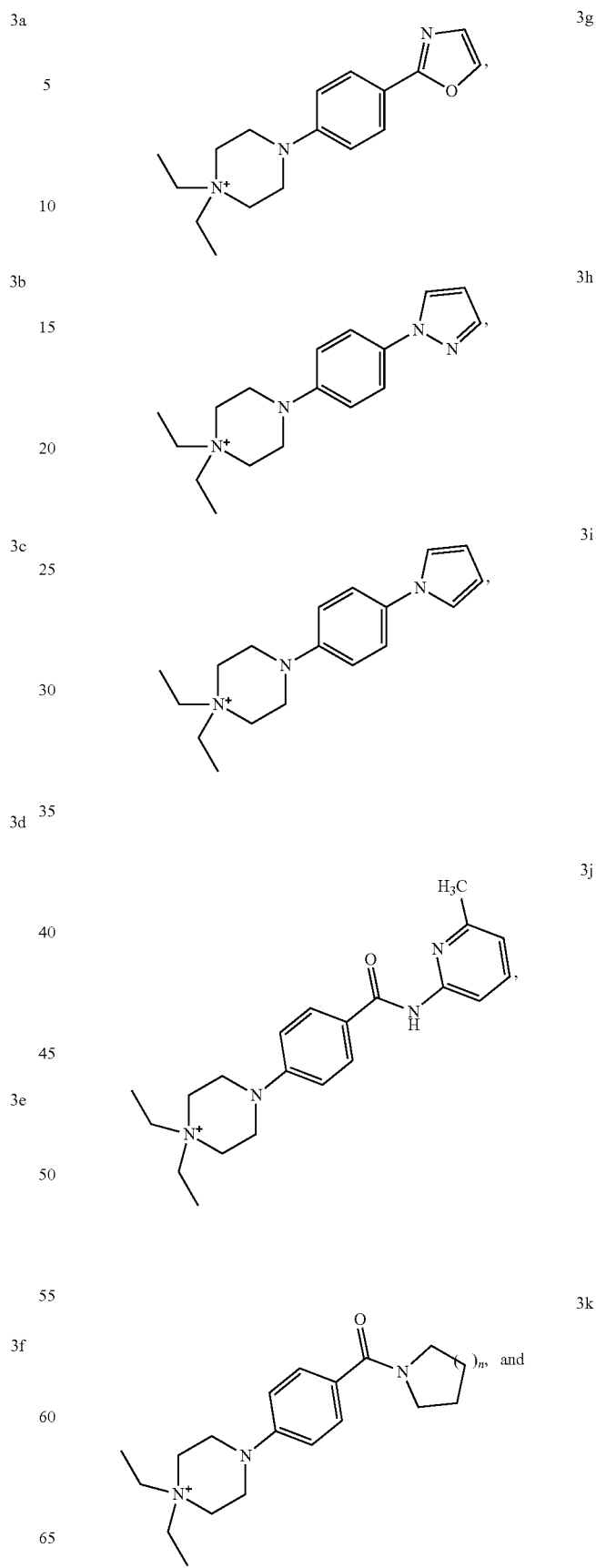

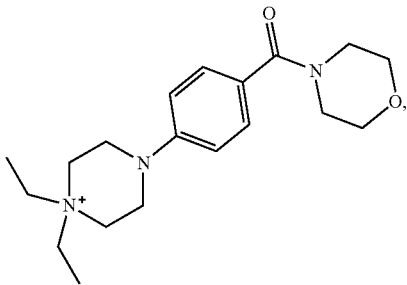

or a salt thereof.

In some embodiments of this aspect of the disclosure, the salt of the para-substituted 1,1-dialkyl-4-phenylpiperazin-1-ium can be an iodide.

In some embodiments of this aspect of the disclosure, the nAChR is an α9, an α9α10, or an α7 nAChR.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 6A-6F illustrate a series of concentration-response curves for reference compound 2 (upper left) and compounds 3b-3f with α7, α9, and α9α10 nAChRs. Experimental data were fit to the Hill curve.

FIG. 8A includes the top pose of compound 3b for reference. The (+) strand and the (−) strand are indicated. FIG. 8B is the same view as in FIG. 8A with a molecular surface on the (−) strand residues. The part of the surface corresponding to the guanidinium group is labeled with an arrow to show its proximity to the carbonyl group of the amide.

FIG. 9A illustrates averaged raw data traces for 100 μM APA-diEPP applications on cells expressing α7 (left, n=7) or α9 (right, n=6) and their respective 60 μM ACh controls. The average normalized responses are shown below along with the structure of APA-diEPP.

FIG. 9B illustrates the concentration-response relationships of APA-diEPP for the activation of cells expressing α7 (net charge, n=7) or α9 (peak currents, n=6). Experiment responses were measured relative to the preceding ACh control responses and then normalized relative to the ratio of the ACh controls to the ACh maximum.

DETAILED DESCRIPTION

Figure 1:
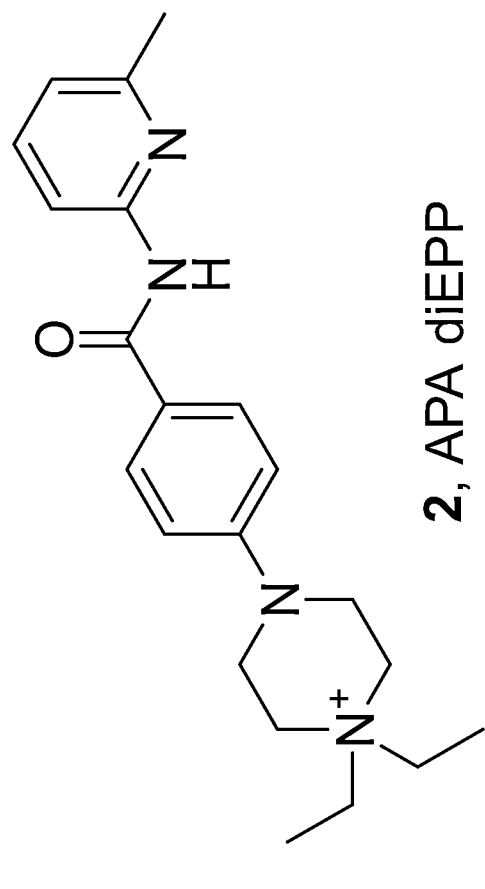
FIG. 1 illustrates structures of previously characterized phenylpiperaziniums.
Figure 1:
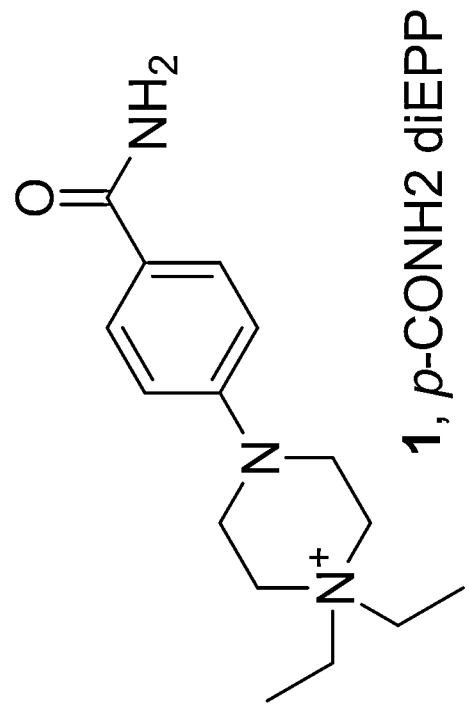

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Abbreviations nAChR, nicotinic acetylcholine receptor; diEPP, N,N-diethyl-N'-phenyl-piperazine, PAM, positive allosteric modulator, PAM; i.p., intraperitoneal; ADHD, attention deficit hyperactivity disorder; CAP, cholinergic anti-inflammatory pathway; LiHMDS, Lithium hexamethyldisilazide;

Definitions

The term "nicotinic acetylcholine receptors (nAChRs)" as used herein refers to pentameric integral membrane proteins that are members of a family of ligand-gated ion channel receptors, which include the $GABA_A$, glycine, and serotonin $5HT3_A$ and $_B$ receptors. The nAChRs mediate "fast" synaptic transmission on a millisecond time frame, rapidly changing the membrane potential. Each of the five constituent receptor polypeptide subunits share a common motif that includes a large extracellular N-terminal hydrophilic domain, three transmembrane hydrophobic domains (termed M1-M3), an intracellular loop of variable size that contains consensus sequences of amino acids for enzymatic phosphorylation, and a C-terminal M4 transmembrane hydrophobic domain; the M2 transmembrane domains of each of the five receptor polypeptide subunits are aligned to create a potential channel, whose opening is gated by acetylcholine. These receptors are assembled from an extensive family of subunits. In vertebrates, the 17 nAChR subunits ($\alpha1$-$\alpha10$, $\beta1$-$\beta4$, $\gamma$, $\delta$, and $\epsilon$) can assemble into a variety of pharmacologically distinct receptor subtypes. There are muscle-type nAChRs and neuronal nAChRs. There is considerable diversity among the sub-family of neuronal nAChRs.

The term "alkyl", either alone or within other terms such as "thioalkyl" and "arylalkyl", as used herein refers to a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. An alkyl radical may be h the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

An aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, —$CH_2CH_2$—S(=O)—$CH_3$, and —$CH_2CH_2$—O—$CH_2CH_2$—O—$CH_3$. Up to two heteroatoms may be consecutive, such as, for example, —$CH_2$—NH—$OCH_3$, or —$CH_2$—$CH_2$—S—S—$CH_3$.

A "cycloheteroalkyl" ring is a cycloalkyl ring containing at least one heteroatom. A cycloheteroalkyl ring can also be termed a "heterocyclyl," described below.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "substituted" as used herein refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents include F, Cl Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', CNH)N(R')$_2$, C(O)N(OR')R', or C=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3$.sup.+, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

An "ammonium" ion includes the unsubstituted ammonium ion NH$_4$.sup.+, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$. The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example, sodium, potassium, and the like; with ammonium salts such as NH$_4$.sup.+ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification, or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, .beta.-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium, and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, Remington's Pharmaceutical Sciences (Martin E W, Remington's Pharmaceutical Sciences, Easton Pa., Mack Publishing Company, $19^{th}$ ed., 1995) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Examples of "pharmaceutically acceptable carriers" include any and all solvents, dispersion media, coatings, antibacterial and antifungal agents, isotonic and absorption delaying agents and the like. The use of such media and agents for pharmaceutical active substances is well known in the art. In one embodiment, the pharmaceutically acceptable carrier is a sterile, fluid (e.g., liquid or gas) preparation rendering the pharmaceutical composition suitable for injection or inhalation. Except as far as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The methods and compositions of the invention may incorporate additional pharmacologically active agents (such as for adjunctive therapy). For example, the additional pharmacologically active agent can be co-administered consecutively or simultaneously (e.g., in the same formulation or different formulations.

Modulation of neuronal nAChR activity in response to contact with the compounds of the present disclosure or a pharmaceutically acceptable salt thereof can involve comparison to a control. One type of a "control" cell or "control" culture is a cell or culture that is treated substantially the same as the cell or culture exposed to the test compound, except the control cell or culture is not exposed to the test compound (the compounds of the present disclosure or a pharmaceutically acceptable salt thereof). For example, in methods that use voltage clamp electrophysiological procedures, the same cell can be evaluated in the presence and absence of the compounds of the present disclosure or a pharmaceutically acceptable salt thereof, by merely changing the external solution bathing the cell. Another type of "control" cell or "control" culture may be a cell or a culture of cells which are identical to the transfected cells, except the cells employed for the control culture do not express functional human neuronal nicotinic AChRs. In this situation, the response of the test cell to the or pharmaceutically acceptable salt thereof is compared to the response (or lack of response) of receptor-negative (control) cell to the or pharmaceutically acceptable salt, when cells or cultures of each type of cell are exposed to substantially the same reaction conditions in the presence of compound being assayed.

The terms "co-administration" or "co-administered" as used herein refer to the administration of at least two compounds or agent(s) or therapies to a subject.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

Compounds of the disclosure can be prepared using reactions and methods generally known to the person of ordinary skill in the art, having regard to that knowledge and the disclosure of this application including the Examples. The reactions are performed in solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the disclosure. It will also be recognized that another major consideration in the development of a synthetic route is the selection of the protecting group used for protection of the reactive functional groups present in the compounds described in this disclosure. An authoritative account describing the many alternatives to the skilled artisan is Greene and Wuts (Protective Groups In Organic Synthesis, Wiley and Sons, 1991).

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The terms "treatment", "treating", and "treat" as used herein refer to acting upon a disease, disorder, or condition with composition or pharmaceutical composition of the present disclosure to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of the composition or pharmaceutical composition of the present disclosure to provide a pharmacologic effect, even in the absence of a disease or condition. For example, "treatment" encompasses delivery of the composition or pharmaceutical composition of the present disclosure that provides for enhanced or desirable effects in the subject (e.g., reduction of disease symptoms, etc.).

The term "agonist" as used herein refers to a compound or molecule, including but not limited to, peptides, oligopeptides, and small molecules, variants, and derivatives thereof that may interact with a receptor of a cell, thereby inducing an increase in a biochemical or physiological activity attributable to the receptor. The agonist may be, but is not limited to, a natural ligand effector of the receptor, an analog or a mimetic and the like thereof.

The term "antagonist" as used herein refers to a compound or molecule, including but not limited to, peptides, oligopeptides, and small molecules, variants, and derivatives thereof that may interact with a receptor of a cell, thereby inducing a decrease in a biochemical or physiological activity attributable to the receptor. The agonist may be, but is not limited to, a natural inhibitor of the receptor, an analog or a mimetic and the like thereof.

Discussion

The present disclosure provides embodiments of novel para-substituted 1,1-dialkyl-4-phenylpiperazin-1-ium iodides and which have been synthesized and their electrophysiology activities for α9, α9α10, and α7 nAChRs compared. The para position contained alkyl or aryl amides, or heterocyclic isosteres for the amide, and the alkyl groups were varied at the ammonium piperazine nitrogen to see if compensatory changes in size at this position of the molecule impacted function. The compounds were characterized with two-electrode voltage-clamp measurements on Xenopus oocytes expressing nAChRs. In general, compounds were more potent for α9-containing receptors than for α7, and most were either full or strong partial agonists for α9-containing nAChR.

One advantageous compound of the disclosure is 1,1-diethyl-4-(4-(pyridin-2-ylcarbamoyl)phenyl)piperazin-1-ium iodide (3c), an efficacious agonist for α9α10 heteromeric receptors with 10-fold better potency relative to α9 homomers. While, in general, the compounds retained high efficacy for α9 nAChR, 4-(4-(1H-pyrrol-1-yl)phenyl)-1,1-diethylpiperazin-1-ium iodide (3i) showed reduced efficacy for both α9* and α7 receptors, likely due to a lack of hydrogen bonding capability. In addition to providing a roadmap for further development of new therapeutics for α9* receptors, these α9-selective compounds will be advantageous for distinguishing the differential roles of α7 and α9 nAChRs in inflammatory signaling.

Embodiments of the present disclosure provide for N,N diethyl-N'phenylpiperazine α7 and α9 nicotinic acetylcholine receptor agonists and antagonists. Two reference compounds (FIG. 1), 4-(4-carbamoylphenyl)-1,1-diethylpiperazin-1-ium iodide (1, p-CONH2 diEPP) and 1,1-diethyl-4-(4-((6-methylpyridin-2-yl)-carbamoyl)phenyl)piperazin-1-ium iodide, (3j, APA-diEPP), which is a derivative of the simpler amide 1 were useful controls. 1 was a full α9 agonist with 66-fold greater potency for α9 than for α7. The carboxamide derivative 3j was also a full α9 agonist with 10-fold greater potency for α9 than for α7. Thus, α9 tolerates the addition of the picolyl group to the amide.

There are few reports on small molecules as full and selective agonists for α9 and α9α10. Now identified are promising agonists with activities and selectivities for targeting α9 and α9α10 over α7 nAChR generated by modifications of a core N-phenylpiperazine scaffold associated with α7 silent agonism.

The data suggest that a hydrogen bond accepting heterocycle at the para position of the phenyl ring, i.e. 1,1-diethyl-4-(4-(oxazol-2-yl)phenyl)piperazin-1-ium iodide, 3g, has strongly diminished activity at α7 and has submicromolar potency with full agonism at α9 nAChR. Changes in the steric bulk at the ammonium nitrogen of the core piperazine appeared to be an important variable that impacted the relative discrimination between α9 and α9α10 receptors and thus bears further investigation. The pyridyl ring of reference compound 3j does not appear to be required for activity, as a phenyl substitution produced a compound with nearly identical activity. In general, consistent with earlier work (Papke et al., (2022) ACS Chem. Neurosci. 13: 624-637), variation of the group at the para position of the core phenyl piperazine is differentially impacting the activity profiles at different nAChR, and that the activity profiles of specific compounds are affected by the potential for hydrogen bond formation within the orthosteric binding site.

The docking data indicated residue R113 for follow-up site-directed mutagenesis to confirm this interaction. The results are also advantageous for the enablement of the ability to design new compounds that will target α9-containing subtypes through identifying specific structural epitopes that would selectively increase or decrease activity, thus enlarging the scope of pharmacological agents available for the investigation of α9 and α9α10 nAChR functions. This may include applications for improving function in the auditory system. Additionally, while there is evidence for both α7 and α9* receptors being potential targets in CAP (Toma et al., (2020) Curr. Top Behav. Neurosci. 45: 153-166; Bagdas et al., (2018) Curr. Neuropharmacol. 16: 415-425; Piovesana et al., (2021) Int. J. Mol. Sci. 22), the details of how these receptors should be targeted remain unclear. It has been suggested that desensitizing (i.e. silent) α7 agonists is more effective than highly efficacious agonists in reducing inflammatory or neuropathic pain, and study compound 3i might fit this category. The most effective way to target α9* to alleviate inflammatory pain remains somewhat uncertain. While studies with conotoxins that are α9 antagonists have suggested that α9 receptors should be targeted with antagonists, it is unclear that conotoxins are behaving as simple antagonists. Other cell-based assays have shown that both the unconventional α9 agonist phosphocholine, and pCF3-diEPP, an α9 partial agonist, structurally related to the study compounds, mediate α9-dependent anti-inflammatory activity (Richter et al., (2022) Front. Cell Neurosci. 16: 779081). Therefore, the varying profiles reported for the study compounds, represented by compounds 3h, and 3i, as discussed above, will provide a new array of precise tools for discriminating between the role of α7 vs α9 receptors in mediation of cholinergic anti-inflammatory pathways.

Figure 3:
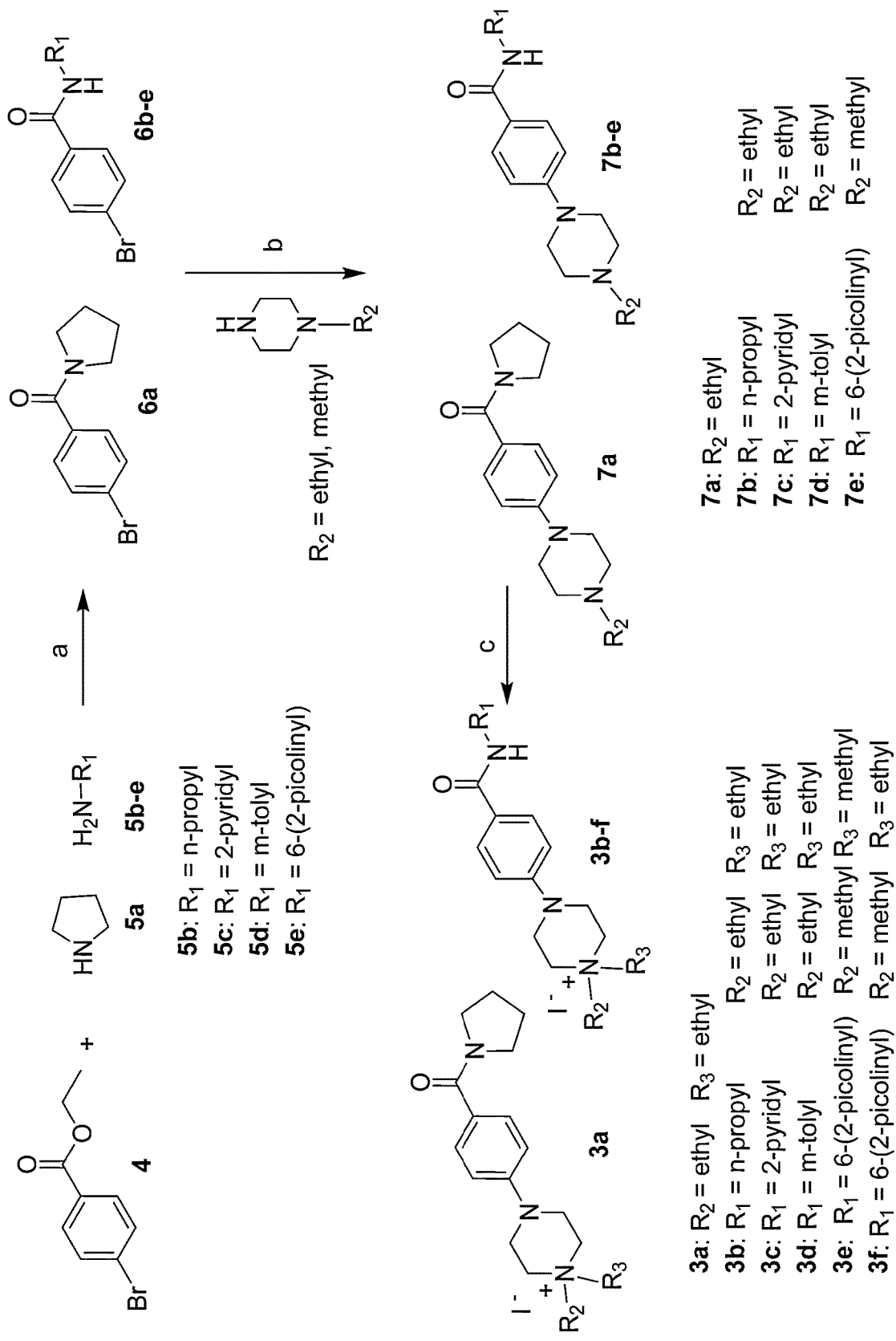
FIG. 3 illustrates Scheme 1 for the synthesis of 1,1-dialkyl-4-(substituted aryl/alkyl)carbamoyl) phenyl)piperazinium iodides of the disclosure. Reagents and conditions: (a) LiHMDS [1.0M in THF] (3.0 equiv), r.t, 24 h, under Ar; (b) [Pd$_2$(dba)$_3$] (10 mol %), cesium carbonate (2.0 equiv), BINAP (20 mol %), N-ethylpiperazine or N-methylpiperazine (4 equiv.), dioxane, 8 h, 90° C. (c) iodoethane or iodomethane, THF, 25° C., 2-24 h.
Figure 4:
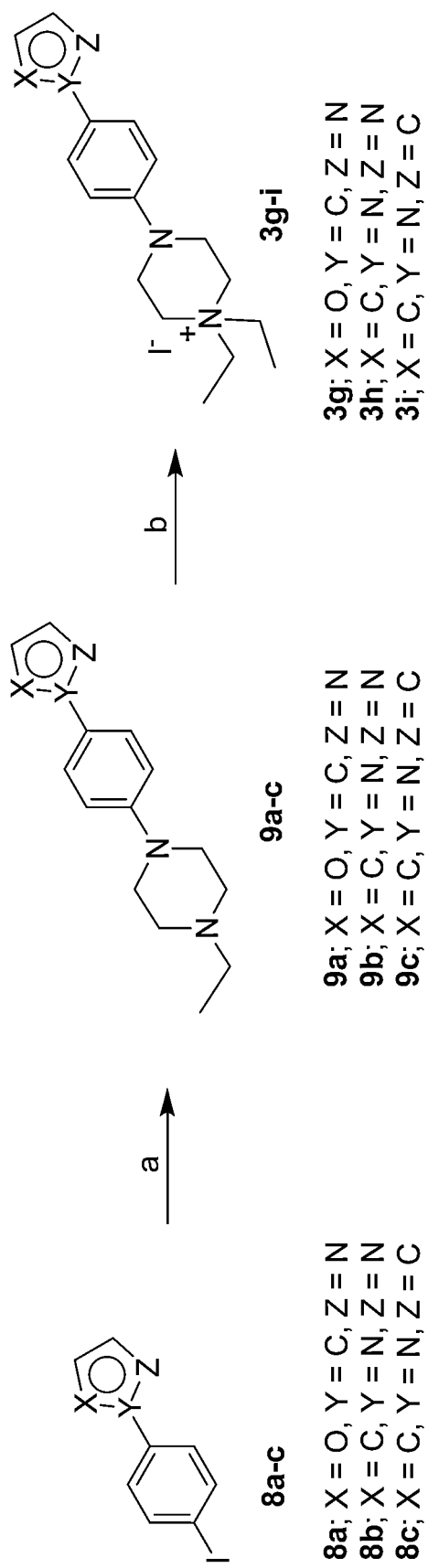
FIG. 4 illustrates Scheme 2 for the synthesis of -(4-(heteroaryl)phenyl)-1,1-diethylpiperazinium iodides. Reagents and conditions: (a) [Pd$_2$(dba)$_3$] (10 mol %), cesium carbonate (2.0 equiv), BINAP (30 mol %), N-ethylpiperazine, dioxane (2 mL), 48 h, 120° C. (b) iodoethane, THF, 25° C., 48 h.

The success of compound 3j as an α9 agonist led us to consider other amides and analogs with the goal of developing additional compounds selective for α9* receptors, and to define the requirements and limitations for compounds in this functional class. It was considered how variation of the hydrogen bonding ability of the amide, amide isosteres, and size of the group(s) on the amide nitrogen might influence activity towards α9 homomeric receptors vs α9α10 receptors or α7 nAChR. Given that the size of the group on the amide nitrogen was being varied, it was determined if smaller groups on the ammonium nitrogen might have compensatory, synergistic, or antagonistic effects when a large amide group was part of the molecule. The core hypothesis of this work is that it is possible to define the extent to which a phenylpiperidine scaffold can be optimized for α9* selectivity. If successful, this would provide new tools to help unravel the complex role(s) that nAChR play in auditory and or anti-inflammatory processes. the set of compounds presented in FIG. 2 were, therefore, synthesized to address these questions. Compound 3a removes hydrogen bond donation from the amide, and adds a cyclic alkyl structure that makes it intermediate in size between 1 and 2. Compound 3b has a short hydrophobic tail and can donate a single hydrogen bond. Compounds 3c,d are analogs of 2 that probe for the importance of the picoline methyl group or nitrogen atom, respectively. Compounds 3e,f are analogs of 2 that reduce the steric bulk around the ammonium nitrogen and 3g-i are heterocyclic amide isosteres for the carboxamide of 1 and probe for the importance of hydrogen bond acceptor behavior of the amide group. *Chemistry*: The general approaches used for the synthesis of N,N-dialkyl-4-(substituted aryl/alkyl)carbamoyl)phenyl)piperazinium iodides (3a-f) and 4-(4-(heteroaryl)phenyl)-N,N-dialkyl piperazinium iodides (3g-i) are depicted in Schemes 1 and 2 as shown in FIGS. 3 and 4, respectively. Amidation of p-bromo ethylbenzoate 4 (Scheme 1, FIG. 3) formed 4-bromo-N-(aryl)benzamides (6a-e) by acyl substitution with amines (5a-e). These reactions proceeded in excellent 90-95% yield at room temperature. This transition-metal-free amidation was conducted using alkyl or arylamines (2.0 equiv), Lithium hexamethyldisilazide (LiHMDS) 3.0 equiv, as a base and THF as a solvent at ambient conditions in the presence of argon. It is noteworthy that the reactions proceeded rapidly and in high yields. The second step was the key step in the synthesis i.e., the C—N cross-coupling reaction for N-arylation of ethylpiperazine or methylpiperazine utilizing 4-bromo-N-(aryl)benzamides (6a-e), leading to the formation of 4-(4-ethylpiperazin-1-yl)-N-alkyl/aryl benzamides (7a-e). As previously described (Papke et al., (2022) *ACS Chem. Neurosci.* 13: 624-637), Buchwald-Hartwig C—N cross-coupling reactions were superior to Ullman chemistry, when the coupling targets included amide functionality. Initially palladium diacetate (10 mol %) and (2,2'-bis(diphenylphosphino)-1,1'-binaphthyl) ligand (BINAP) (20 mol %) in toluene were used. The reaction failed to complete, even after 4 days, leading to exceptionally low yields. Tetrakis(triphenylphosphine)palladium$^{(0)}$ [palladium tetrakis] (10 mol %) was used instead of Pd(OAc)$_2$, using sodium tertiary butoxide (2 equiv) as a base in toluene; however, it ended up with a number of impurities that could not be separated even by column chromatography. Finally, the reaction utilizing 10 mol % of tris(dibenzylideneacetone)dipalladium$^0$ (Pd$_2$(dba)$_3$) in cesium carbonate (2.0 equiv) as a base and BINAP (10-20 mol %) in 1-2 mL of dioxane afforded a good yield (60-78%) of coupled product after purification. Once obtained, the 4-(4-ethylpiperazin-1-yl)-N-alkyl/aryl benzamides (7a-e) were then converted into the quaternary ammonium salts by alkylation with ethyl iodide or methyl iodide in tetrahydrofuran and then purified by precipitation to afford the N,N-dialkyl-4-(substituted aryl/alkyl) carbamoyl)phenyl)piperazinium iodides (3a-f).

A similar procedure (Scheme 2, FIG. 4) was adopted for synthesis of N,N-diethyl-4-heteroarylphenyl)piperazin-1-ium iodides (3g-i), utilizing N-(4-heteroarylphenyl)-N'-ethylpiperazines (9a-c) with some modifications. The formation of the final products was confirmed by spectroscopic techniques. The formation of compounds 3a-i was confirmed through $^1$H NMR spectroscopy. A triplet for six protons and a quartet of four protons corresponding to 2 methyl groups and 2 methylene groups, respectively, confirmed the desired transformation into N,N-diethyl salts for the compounds 3a-i.

Electrophysiology: Xenopus oocytes were microinjected with RNAs to produce functional nAChR which were characterized by two-electrode voltage-clamp measurements. FIGS. 5A-7D present concentration-response curves for the new compounds evaluated with α7, α9, and α9α10 receptors. Table 1 presents the values for $I_{max}$ and $EC_{50}$ with these receptors and Table 2 summarizes inhibition data for the compounds with heteromeric nAChR.

Figure 5A:
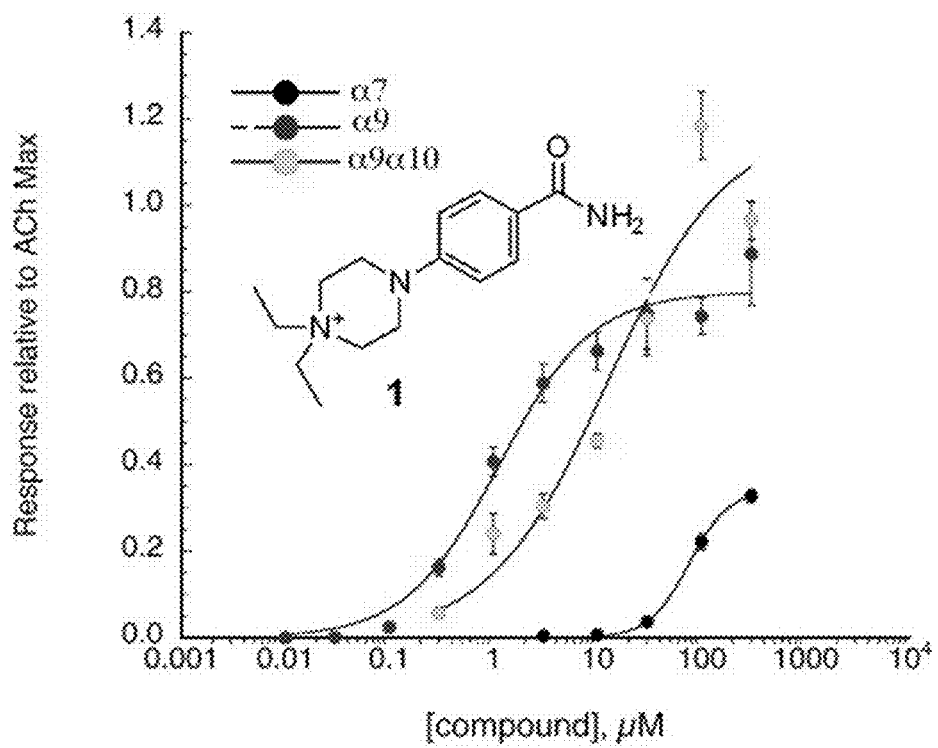
FIGS. 5A-5B illustrate a series of concentration-response curves for compound 3a with α7, α9, and α9α10 nAChR (right). The data for reference compound 1 are shown on the left.
Figure 5B:
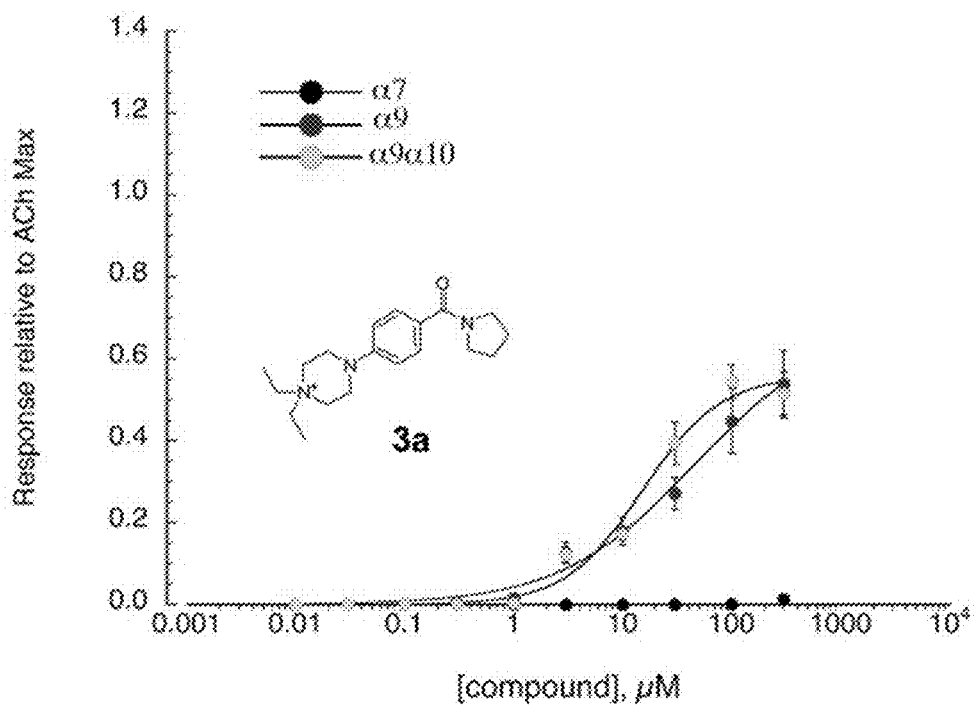
Figure 6D:
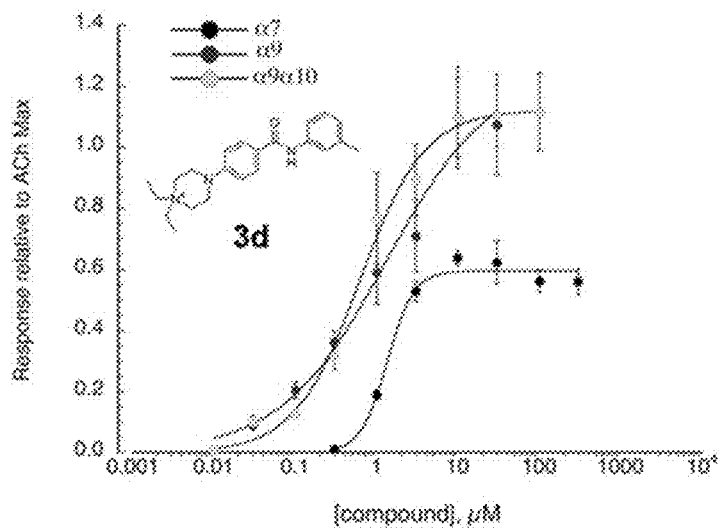
Figure 6E:
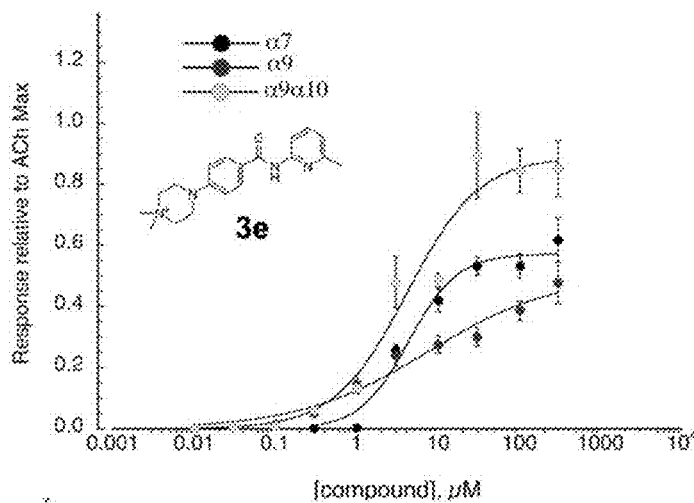
Figure 6F:
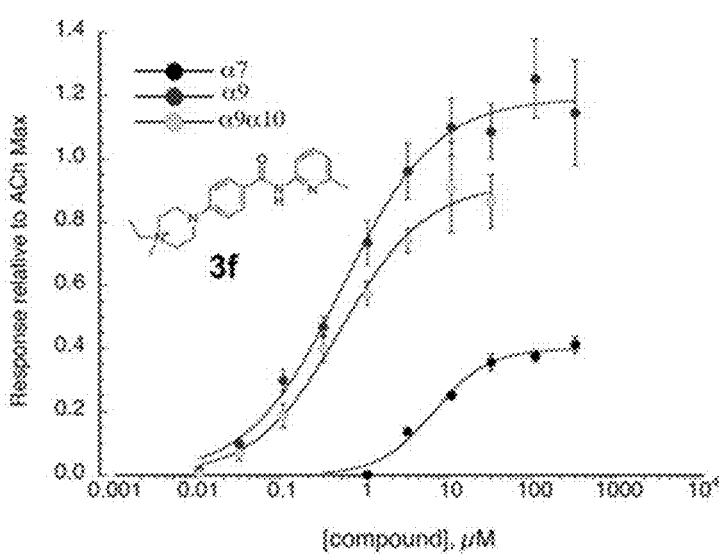
Figure 7A:
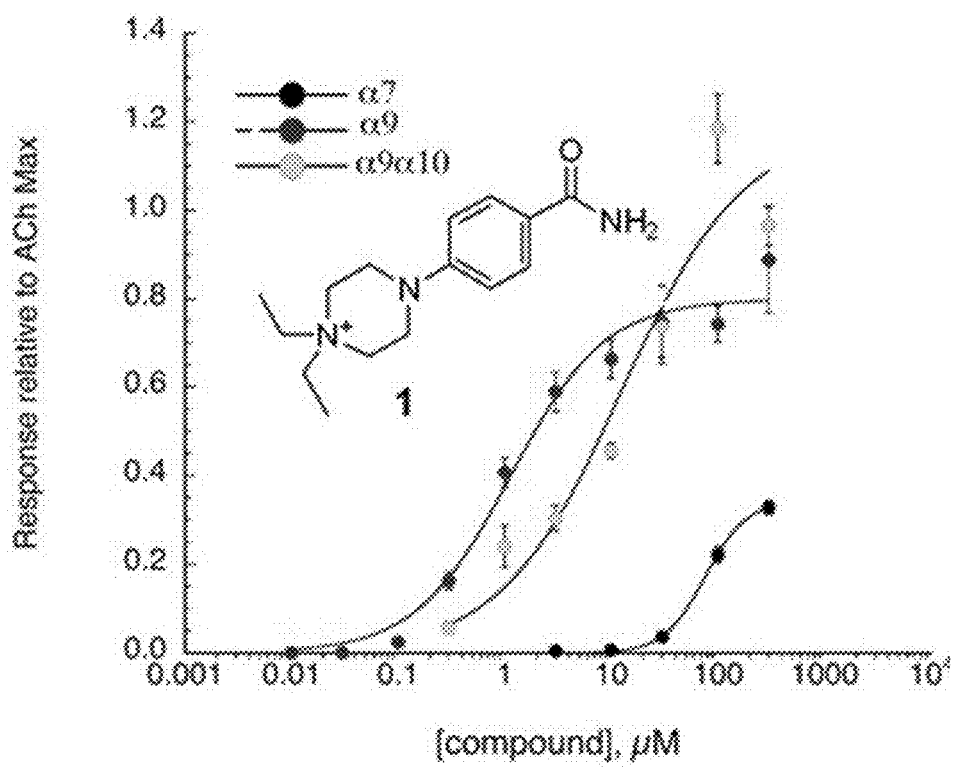
FIGS. 7A-7D illustrate a series of concentration-response curves for reference compound 1 (upper left) and compounds 3g-3i with α7, α9, and α9α10 nAChRs. Experimental data were fit to the Hill curve.
Figure 7B:
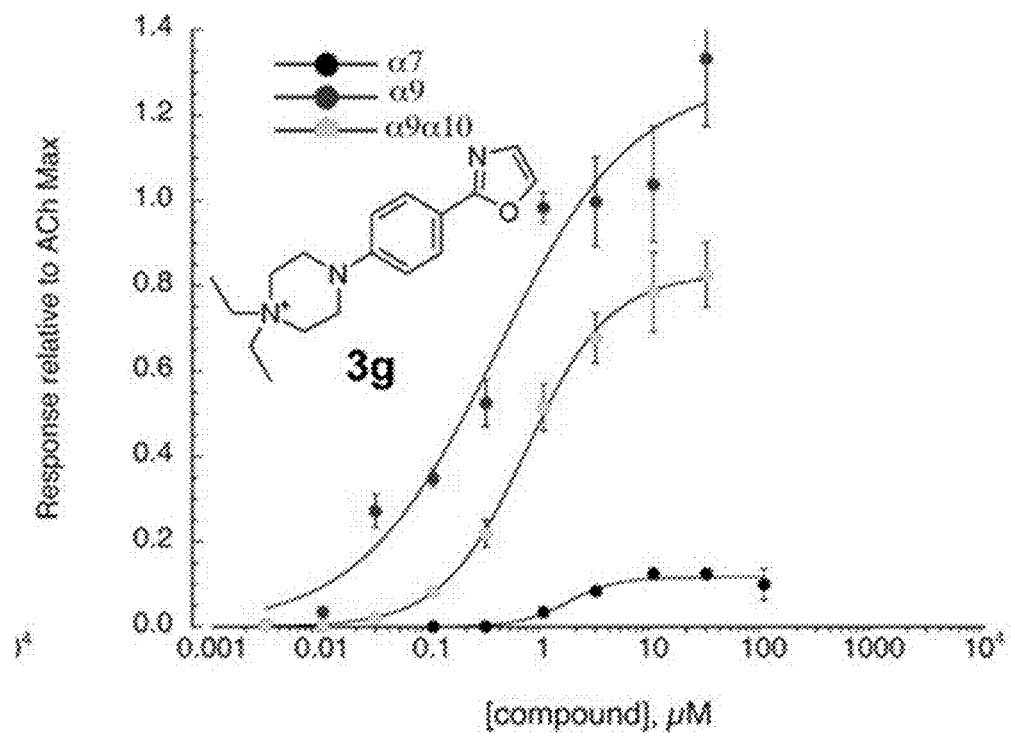
Figure 7C:
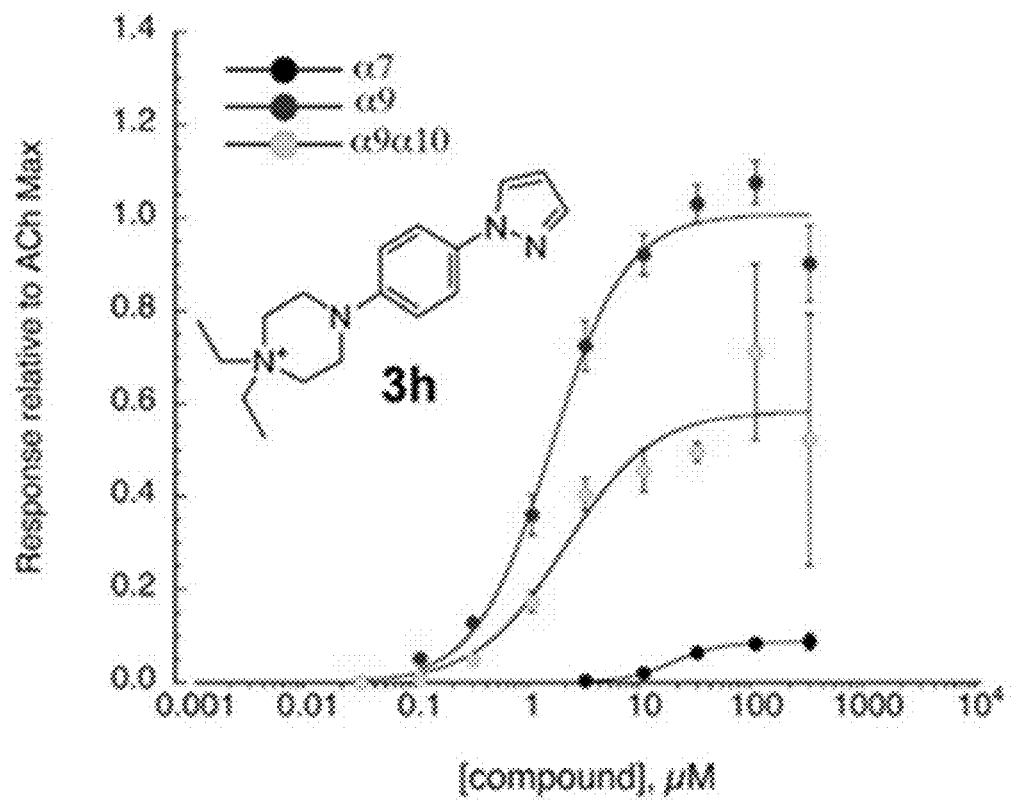
Figure 7D:
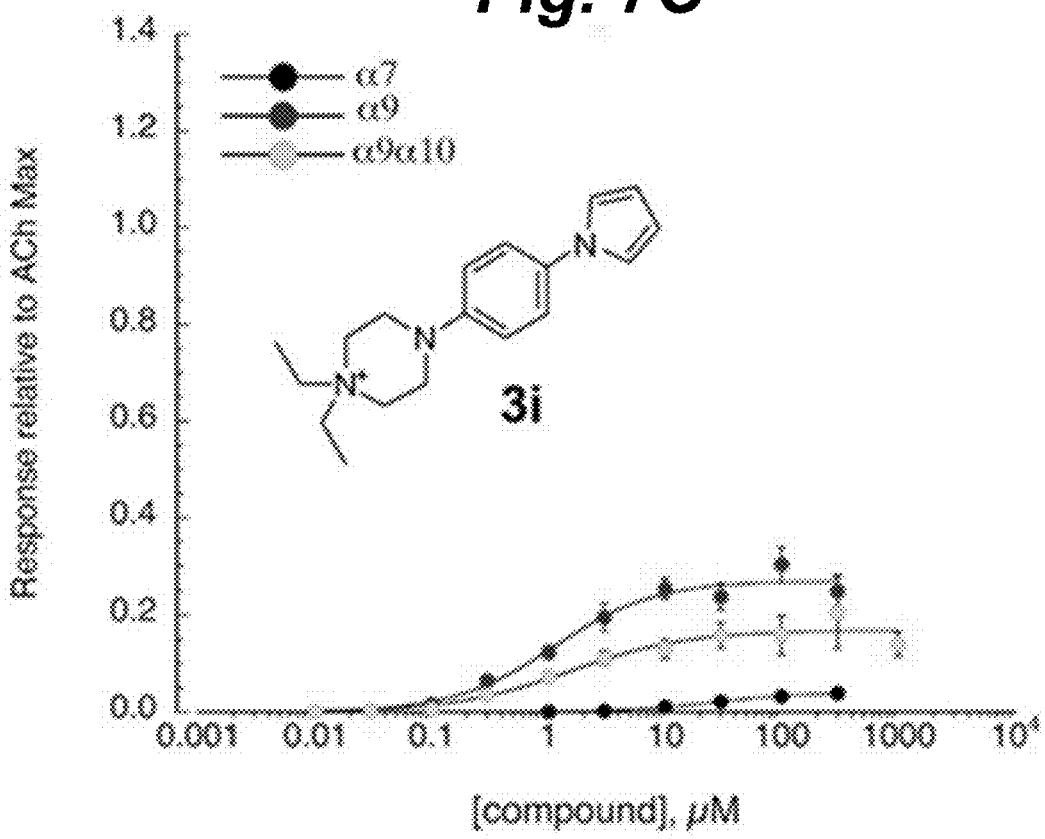

Compound 3a is unique from the other eight compounds in that it is a secondary amide and cannot donate a hydrogen bond. Relative to p-CONH2 diEPP, 1, which has a carboxamide group, compound 3a proved to be both less potent and less efficacious for α9-containing receptors, and it lost agonism for α7 (FIGS. 5A and 5B). Since compound 3a is no longer able to donate a hydrogen bond compared with 1, which in principle can donate two hydrogen bonds, the results support the idea that the loss of hydrogen bond donation was most critical for activity at α7. However, having two alkyl groups on the amide nitrogen, 3a also introduces a steric factor that cannot be discounted as a contributor to the reduced efficacy and potency of the compound.

TABLE 1

$I_{max}$ and $EC_{50}$ values for agonists with α9-containing and α7 nAChR.

| Compound | α9 | | α9α10 | | α7 | |
|---|---|---|---|---|---|---|
| | $I_{max}^a$ | $EC_{50}^b$ | $I_{max}^a$ | $EC_{50}^b$ | $I_{max}^a$ | $EC_{50}^b$ |
| 1 | 0.80 ± 0.03 | 1.15 ± 0.24 | 1.19 ± 0.25 | 13 ± 11 | 0.34 ± 0.01 | 76 ± 2 |
| 2* | 1.06 ± 0.02 | 0.66 ± 0.05 | 0.90 ± 0.02 | 0.98 ± 0.09 | 0.42 ± 0.02 | 6.4 ± 1.4 |
| 3a | 0.69 ± 0.09 | 45 ± 22 | 0.56 ± 0.04 | 15 ± 3.1 | 0.06 ± 0.11 | 500 ± 500 |
| 3b | 1.13 ± 0.15 | 9 ± 6 | 0.79 ± 0.13 | 11 ± 6 | 0.38 ± 0.09 | 280 ± 240 |
| 3c | 1.18 ± 0.39 | 18 ± 36 | 0.94 ± 0.04 | 1.18 ± 0.26 | 0.46 ± 0.08 | 26 ± 20 |
| 3d | 1.25 ± 0.14 | 1.28 ± 0.62 | 1.12 ± 0.03 | 0.61 ± 0.08 | 0.60 ± 0.02 | 1.3 ± 0.1 |
| 3e | 0.51 ± 0.07 | 7 ± 6 | 0.89 ± 0.07 | 4.2 ± 1.5 | 0.57 ± 0.03 | 4.3 ± 1.0 |
| 3f | 1.19 ± 0.03 | 0.51 ± 0.07 | 0.92 ± 0.04 | 0.48 ± 0.09 | 0.40 ± 0.02 | 6.1 ± 1.1 |
| 3g | 1.29 ± 0.13 | 0.38 ± 0.17 | 0.83 ± 0.01 | 0.70 ± 0.03 | 0.12 ± 0.01 | 1.7 ± 0.4 |
| 3h | 1.01 ± 0.04 | 1.49 ± 0.24 | 0.59 ± 0.05 | 2.0 ± 0.8 | 0.088 ± 0.001 | 18 ± 0.60 |
| 3i | 0.27 ± 0.01 | 1.12 ± 0.25 | 0.17 ± 0.01 | 1.5 ± 0.6 | 0.041 ± 0.002 | 27 ± 4 |

$^a I_{max}$ values are presented relative to ACh ($I_{max}$ = 1).
$^b EC_{50}$ values are in units of μM.
See Experimental section for details.
*Data on 2 are taken from Papke et al., (2022) *ACS Chem. Neurosci.* 13: 624-637.

Figure 2:
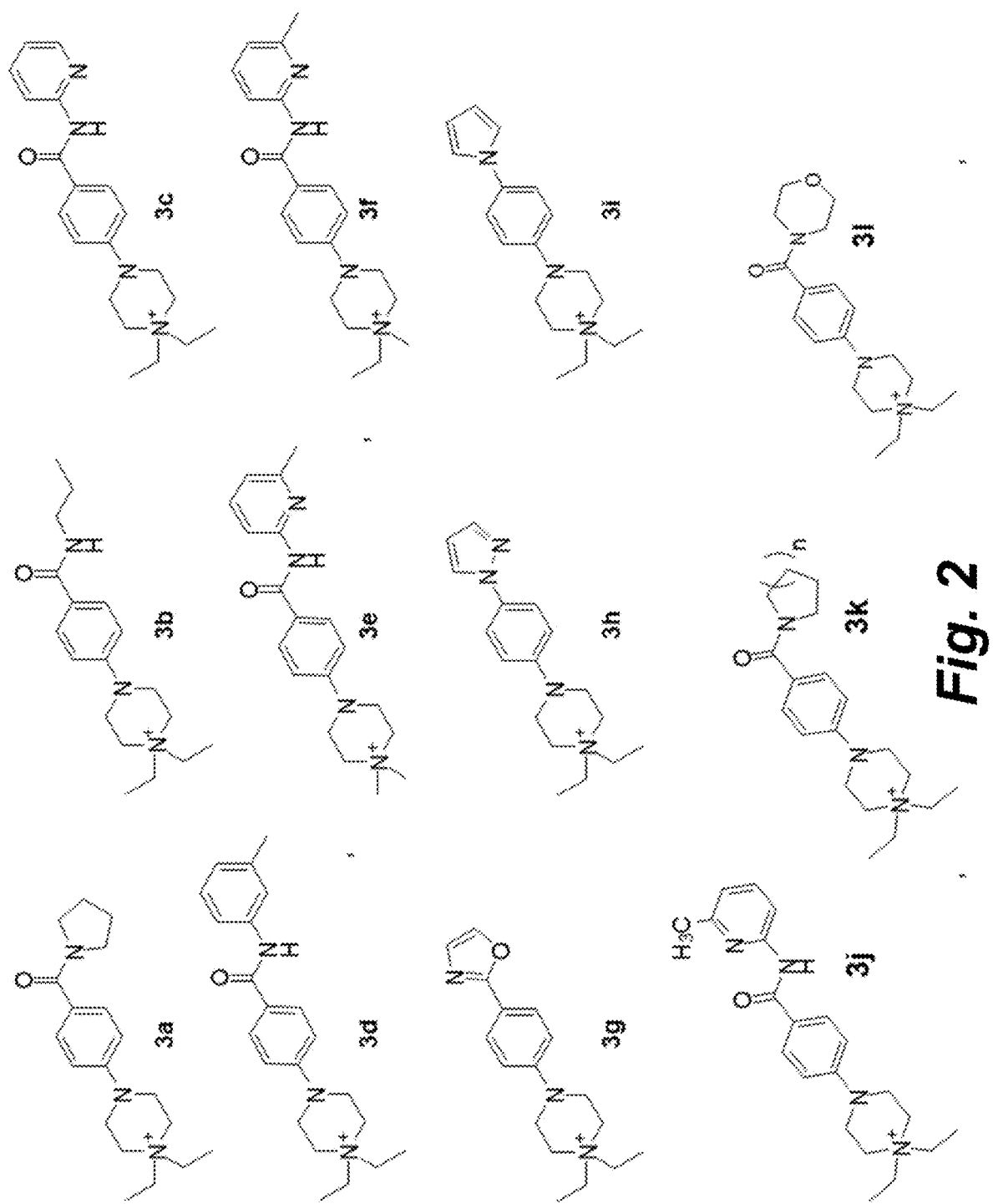
FIG. 2 illustrates the structures of phenylpiperaziniums of the disclosure. All compounds shown are in the iodide form of the ammonium salt.

FIGS. 6A-6F present data for the concentration-response curves for compounds 3b-f (structures as shown in FIG. 2) and the values for $I_{max}$ and $EC_{50}$ are presented in Table 1. All of these compounds have the ability to donate a hydrogen bond at the amide NH group, but vary in either the nature of the N-amide substituent (3b-d) or the size of alkyl groups at the ammonium nitrogen (3e,f). For comparison, concentration-response data are also presented for the reference compound APA-diEPP, 2 (Papke et al., (2022) *ACS Chem. Neurosci.* 13: 624-637). Qualitatively, apart from compound 3e, all compounds in this set showed enhanced efficacy for the α9* receptors in comparison with the α7 receptor, and they tended to be more potent.

Steric bulk at the ammonium group: Compound 3f substitutes one methyl for an ethyl at the ammonium nitrogen of 2, making it smaller in this region. It had slightly better potency towards α9 relative to 2 (0.51±0.07 vs 0.66±0.05 μM) and about twice the potency for α9α10 relative to 2 (0.48±0.09 vs 0.98±0.09). In terms of efficacy, 3f was a full agonist at α9 and almost so for α9α10 ($I_{max}$ values 1.19±0.03 and 0.92±0.04, respectively). This apparent benefit of a smaller ammonium substituent did not extend to the dimethyl analog 3e. In this case, potencies were reduced about 10-fold for either α9-containing receptor, though 3e remained a fully efficacious agonist for α9α10, but a partial agonist for α9. Interestingly, α7 was indifferent to these structural changes at the ammonium group. When one compares 2, 3f, and 3e, which sequentially decrease in size at the ammonium nitrogen, $I_{max}$ and $EC_{50}$ values for α7 remained clustered in the range 0.40-0.57 and 4.3-6.4 μM, respectively. This result suggests that substitution at the ammonium nitrogen may be a useful way to tune for α9α10 selectivity. It should be noted, however, that the relative insensitivity of the α7 responses to steric bulk in this domain was unexpected since an earlier study with simple piperidinium compounds showed a strong effect of increased size of groups on the ammonium, reducing efficacy for α7 channel activation.

It was reported that diM-piperidinium (an analog of 3e), was essentially a full agonist of α7, while diE-piperidinium (an analog of 3d) was an α7 silent agonist, giving responses only when co-applied with the α7 positive allosteric modulator (PAM) PNU-120596. Although the core pharmacophore for all these compounds is the amine on the piperidinium, the addition of bulk to the amine in the form of two ethyl groups converted both diE-Pip and diEPP to silent agonists. However, the data indicate that specific substitutions on the phenyl group of the diEPP compounds can have significant impact on α7 efficacy, suggesting that these distant groups may reposition the amine in the binding pocket in such a way as to restore efficacy.

The nature of the aiylamide: Compounds 3c and 3d are variations on the picolyl group of reference compound 2, APA diEPP. Compound 3c tests for the importance of the methyl group on the pyridine ring, while 3d keeps the methyl but removes the pyridyl nitrogen and is thus probative for the significance of a pyridine ring vs a benzene ring.

Inspection of the concentration-response curves for 3c (FIG. 6C) reveals a trend, specifically that the concentration-response curve for 3c with α9 vs α9α10 shows a selective shift toward lower potency only for α9, not α9α10. Accordingly, one aspect of the present disclosure encompasses embodiments of the compounds wherein the size and substituents of the arylamide aryl ring are varied. This suggests that it may be possible to pharmacologically distinguish between α9 and α9α10 receptors by variation of the size and substituents of the arylamide aryl ring.

The two compounds 3c and 3d were unremarkable in their activity towards α7, in comparison to compound 2, all acting as partial agonists with micromolar $EC_{50}$ values. Compound 3d is the analog of 2 that replaces the pyridine ring with a phenyl ring. Inspection of Table 1 and FIG. 6D reveals that 3d is quite similar in its properties to the reference compound 2, suggesting that the pyridyl nitrogen plays an insignificant role in the activity of the compounds.

Amide group isosteres: Compounds 3g-3i (FIG. 2) replace the carboxamide group of p-CONH2 diEPP, 1, with different heterocycles that vary the position of nitrogen or contain an oxygen with which different patterns of hydrogen bonding may occur when receptor bound. Oxazole 3g maintains the arrangement of the N and O atoms of a carboxamide but can only accept hydrogen bonds. Pyrazole 3h can only accept a single hydrogen bond, while pyrrole 3i would not be able to hydrogen bond. All three are close in size. FIGS. 7A-7D present the concentration-response curves for the compounds 3g-3i compared with the data for the reference compound 1. Parameters derived from these curves are found in Table 1.

It is apparent from inspection of the data in FIGS. 7A-7D that 3g-3i had low efficacy for α7 with low to mid micromolar potencies. On the other hand, 3g had submicromolar potency for the α9-containing receptors, being a full agonist for α9 and a strong partial agonist for α9α10 receptors ($I_{max}$=1.29±0.13 and 0.83±0.01, respectively).

Compound 3h was a full agonist for α9, but a partial agonist for α9α10. Relative to 3g, it lost potency for both α9 and α9α10 receptors by a factor of 3. Both 3g and 3h were very weak partial agonists of α7, and in comparing 3g with 3h, a 10-fold loss of potency for 3h ($EC_{50}$s 1.7±0.4, 18±0.60, respectively) was observed.

Compound 3i lacked the ability to accept a hydrogen bond, and it was a weakened partial agonist for both α9-containing receptors (but not as much impact on potency). This result suggests that hydrogen bond accepting ability is important for the efficacy for 3g and 3h, but less essential for binding. Hydrogen bond accepting ability may therefore be a key part of recognition of the amides in these compounds. However, the findings that compound 3g was active and is not an amide, therefore unable to donate a hydrogen bond, led to the activity of compound 3a (Table 1, FIG. 5A) being reconsidered. It is capable of accepting a hydrogen bond, but not donating a hydrogen bond. It has moderate efficacy at α9 receptors. But the $EC_{50}$ values for 3a were elevated relative to all other compounds, leading to the question of whether high potency has a requirement for H bond donation. The results discussed above for 3g argue that this is not the case. Steric effects associated with a disubstituted amide may be at the root of low potency for 3a, not a lack of hydrogen bond donation.

General features of the α9 receptor orthosteric site: A previously reported α9 homology model (Papke et al., (2022) ACS Chem. Neurosci. 13: 624-637) was used to perform molecular docking of compounds 3a-3i into the receptor to identify specific interactions that may be correlated with activity for the compound series. Compounds 3a-3h docked into the orthosteric site with tightly clustered Glide scores between −8.3 and −6.0 kcal/mol. Interestingly, compound 3i, having the lowest efficacy for all receptors (Table 1), did not produce a low energy orthosteric site pose.

Figure 8A:
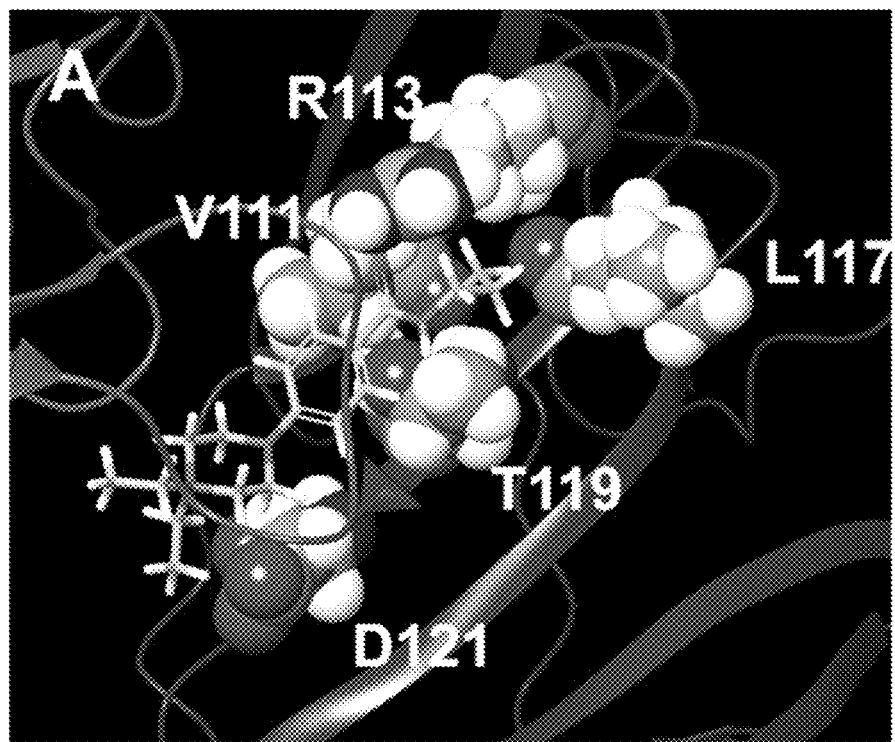
FIGS. 8A-8B illustrate the key residues on the (−) face of the orthosteric site of the α9 nAChR homology model.
Figure 8B:
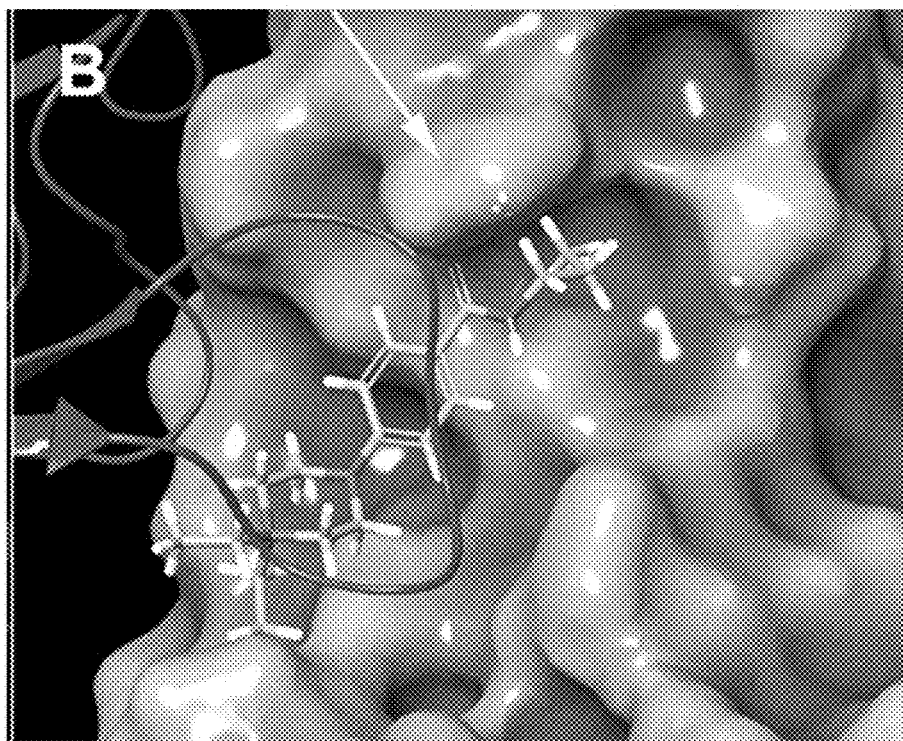

The poses for 3a-h placed the ammonium group under the C-loop in the π-cation box and had, to varying degrees, dipolar interactions with the backbone amide carbonyl of the (+) face W151, a common binding feature of the nAChR. Present in α9 and α10 but not α7, the D121 carboxylate on the (−) face of the orthosteric binding site also appeared to have electrostatic interactions with the ammonium group with distances between the carboxylate and ammonium centers ranging between 3.7-4.8 Å for compounds 3a-3h (FIG. 8A). An extended binding pocket is created by V111, R113, L117, and T119. FIG. 8B presents a molecular surface in this region to illustrate the shape of the pocket, which is dominated by hydrophobic faces contributed by V111, the side-chain methylene groups of R113, L117, and the side chain γ methyl of T119.

A potential hydrogen bonding partner: A common feature of top poses for most compounds of the disclosure was a likely hydrogen bond between the amide carbonyl (or the heterocyclic O, or N of 3g and 3h) and one of the guanidinium amino groups of R113 on the (−) face (FIG. 8A). The donor/acceptor distances in the top poses for compounds 3b-3h showed a distance of 3.1±0.3 Å. The flexibility of the R113 side chain and the vagaries of docking indicate that this is a viable proposal on the basis of the close distance. Compound 3a bound with a different pose, in which the 5 hydrophobic atoms of the amide pyrrolidine ring were in Van der Waals contact with the face of the R113 guanidinium group; this pose places its carbonyl oxygen remote from R113, unable to hydrogen bond with it. This type of non-polar interaction with arginine guanidinium groups has 10 been characterized [Armstrong, 2016 #6220]. Compound 3i, lacking a hydrogen bond acceptor did not dock in the orthosteric site.

No poses in which the amide NH group of compounds 3b-3f had a hydrogen bonding partner were seen, suggesting 15 co-applied with 10 µM PNU-120596 (Table 2). The co-application of ACh with PNU-120596 produced peak current responses that were 21.6±4.7 times larger than the responses to ACh alone. The $\alpha 7$ responses to the test compounds co-applied with PNU-120596 were relatively small and generally in proportion to the $\alpha 7$ activity when applied alone. However, 3h, and 3i, which had relatively low $\alpha 7$ efficacy when applied alone, gave relatively large responses when co-applied with PNU-120596 (approximately 4 and 2 times the ACh controls, respectively), bringing them close to the criteria for silent agonism [Quadri, 2016 #5368]. In the case of 3h, this $\alpha 7$ activity might synergize with $\alpha 9^*$ agonism in regard to CAP, while with 3i there would be less chance of this interaction.

TABLE 2

Responses to the drugs at 30 µM co-applied with 10 µM PNU-120596 and normalized to the responses 30 µM ACh co-applied with 10 µM PNU-120596.

| drug | ACh | Compound | | | | | | | | | | |
| --- | --- | --- | --- | --- | --- | --- | --- | --- | --- | --- | --- | --- |
| | | 1 | 2 | 3a | 3b | 3c | 3d | 3e | 3f | 3g | 3h | 3i |
| PNU | 1.00 | 0.18 | 0.17 | 0.01 | 0.19 | 0.12 | 0.17 | 0.16 | 0.13 | 0.05 | 0.17 | 0.08 |
| SEM | 0.33 | 0.03 | 0.01 | 0.00 | 0.01 | 0.01 | 0.01 | 0.03 | 0.01 | 0.00 | 0.02 | 0.00 |
| *$\alpha 7\ I_{Max}$ | 1 | 0.34 | 0.42 | 0.06 | 0.38 | 0.46 | 0.6 | 0.57 | 0.4 | 0.12 | 0.088 | 0.041 |

*taken from Table 1 this type of interaction is not operative in molecular recognition. On the basis of these observations and the experimental results (Table 1) for 3a (low potency) and 3i (low efficacy) may be related to their lack of hydrogen bonding accepting interactions with R113, and hydrogen bond accepting functionality is identified as useful for incorporation into $\alpha 9$ ligands at the para position of the phenyl piperazine scaffold.

Additional observations from docking: Compounds 2 and 3c are related by the difference of a single methyl group, and experimentally, 3c may be less potent, based on a shift of the concentration-response curve for $\alpha 9$ compared to $\alpha 9=10$, as shown in FIG. 6C. The best poses for compound 2 placed the picoline methyl group in a solvent exposed position, but the Glide score for a pose that placed the methyl group in contact with L117 and the side chain of R113 was within 1.2 kcal/mol of the best pose. There is, therefore, support that hydrophobic substituents may be useful to tailor interactions at the (−) interface of the $\alpha 9$ homopentamer.

The best poses of any of the pyridine ring-containing compounds (3c, 3e, and 3f) placed the pyridyl nitrogen in a solvent exposed position. This agrees with the experimental observation that removing the pyridyl nitrogen (compound 3d) made only a minor difference in activity relative to 2 for $\alpha 9$-containing receptors (Table 1).

Silent agonism of $\alpha 7$: The starting point for the early study of $\alpha 9^*$ agonists and antagonists (Papke et al., (2022) *ACS Chem. Neurosci.* 13: 624-637) was a previously characterized family of putative $\alpha 7$ silent agonists, compounds that produce relatively little $\alpha 7$ channel activation when applied alone but do induce a PAM-sensitive desensitized state. As noted earlier, this PAM-sensitive desensitized state may have metabotropic activity in CAP (Bagdas et al., (2018) *Curr. Neuropharmacol.* 16: 415-425). The compounds of the disclosure, which all had relatively low efficacy for $\alpha 7$ when applied alone, activate the receptors when co-applied with the $\alpha 7$ PAM PNU-120596. Those responses were then compared to the activation produced when 30 µM ACh was Initial profiling against heteromeric receptors: The test compounds for their ability to activate or inhibit other nAChR subtypes were evaluated. Agonist activity was evaluated by applying the compounds at 100 or 30 µM to human $\alpha 4\beta 2$ and $\alpha 3\beta 4$ as well as to mouse muscle $\alpha 1\beta 1\epsilon\delta$ nAChR expressed in Xenopus oocytes. In no case did the compounds evoke a response as large as 1% of the respective ACh controls (30 µM for $\alpha 4\beta 2$ and $\alpha 1\beta 1\epsilon\delta$, 100 µM for $\alpha 3\beta 4$ receptors), i.e. basically below the limit of detection (data not shown). To evaluate inhibitory activity on the same receptor subtypes, compounds were co-applied with 3 µM of the test compounds, 3 µM being a concentration in the range of the potency for $\alpha 9$ activity. The inhibitory activity was generally low (Table 3).

TABLE 3

Effects of 3 µM co-application on the control ACh responses

| Compound | nAChR | | |
| --- | --- | --- | --- |
| | $\alpha 3\beta 4$ | $\alpha 4\beta 2$ | $\alpha 1\beta 1\epsilon\delta$ |
| 3a | 0.849 ± 0.034 | 0.919 ± 0.022 | 0.541 ± 0.048 |
| 3b | 0.650 ± 0.039 | 0.946 ± 0.032 | 0.709 ± 0.086 |
| 3c | 0.789 ± 0.057 | 0.697 ± 0.027 | 0.506 ± 0.082 |
| 3d | 1.039 ± 0.015 | 0.807 ± 0.048 | 0.555 ± 0.060 |
| 3e | 0.838 ± 0.037 | 0.912 ± 0.038 | 0.709 ± 0.091 |
| 3f | 0.849 ± 0.018 | 0.858 ± 0.045 | 0.413 ± 0.070 |
| 3g | 0.507 ± 0.032 | 0.823 ± 0.043 | 0.353 ± 0.071 |
| 3h | 0.736 ± 0.034 | 0.913 ± 0.026 | 0.590 ± 0.062 |
| 3i | 0.387 ± 0.057 | 0.709 ± 0.086 | 0.691 ± 0.094 |

Figure 9A:
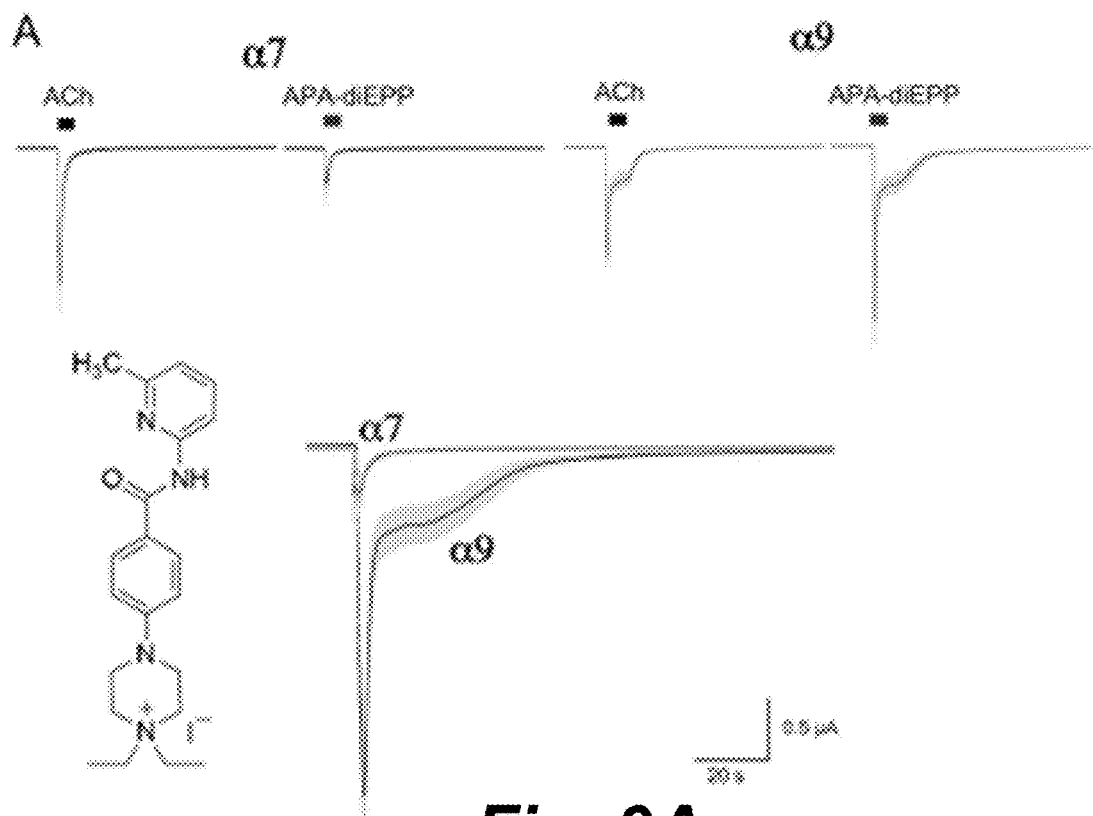
FIGS. 9A and 9B illustrate the characterization of APA-diEPP.
Figure 9B:
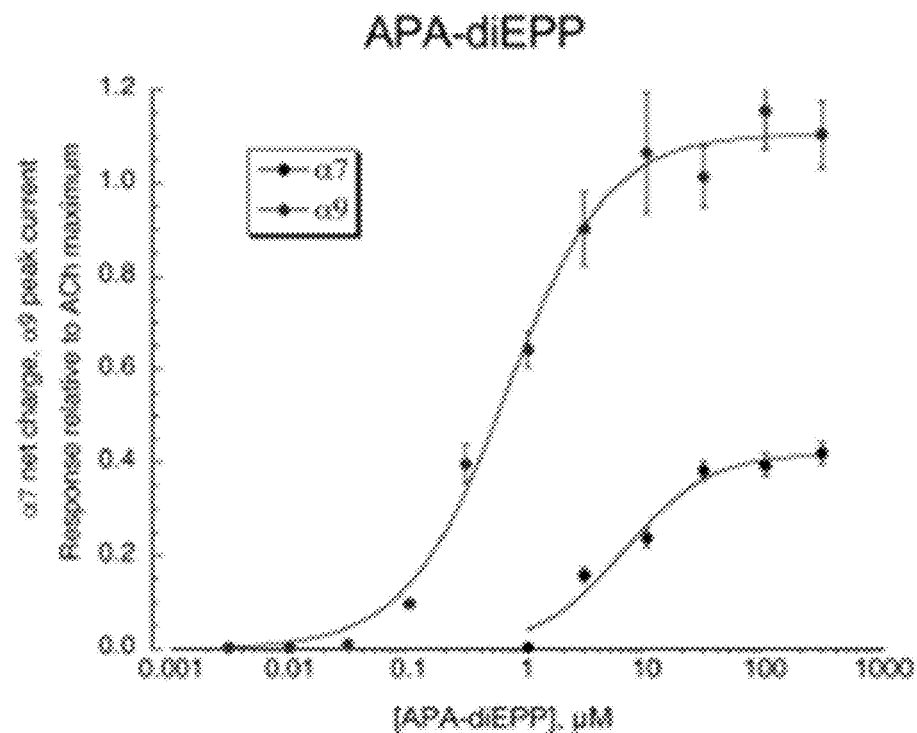
Figure 10:
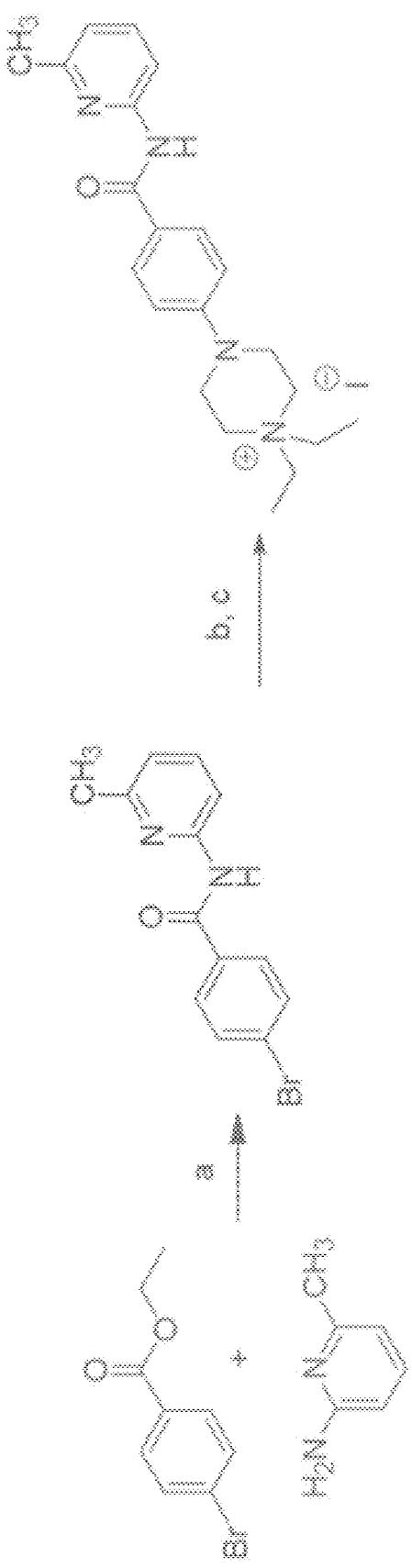
FIG. 10 illustrates the scheme for the synthesis of APA-diEPP.

It was hypothesized that larger substituents on the aryl ring could maintain, and perhaps enhance, selectivity for $\alpha 9$ agonism over $\alpha 7$ activity. This proved to be the case with APA-diEPP, 1,1-diethyl-4-(4-((6-methylpyridin-2-yl)carbamoyl)phenyl)piperazin-1-ium iodide. It was found that it had an approximately 10-fold higher potency for $\alpha 9$ and was a full agonist for this receptor but was only a partial agonist for $\alpha 7$, as shown in FIGS. 9A and 9B.

One aspect of the disclosure, therefore, encompasses embodiments of a para-substituted 1,1-dialkyl-4-phenylpiperazin-1-ium having the formula:

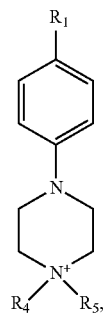

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the para-substituted 1,1-dialkyl-4-phenylpiperazin-1-ium is selected from the group consisting of the formulae:

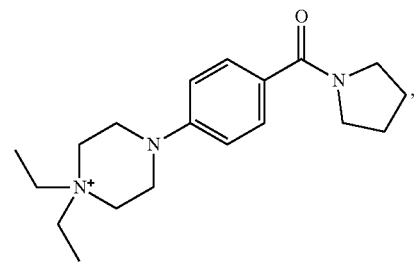

3a

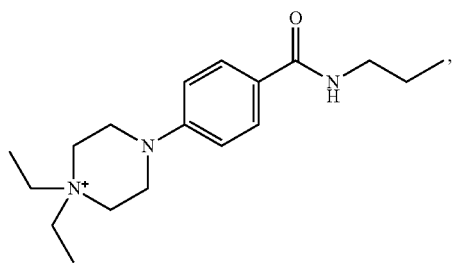

3b

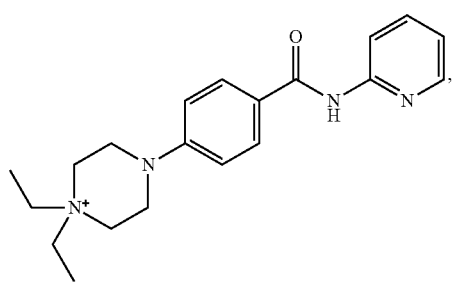

3c

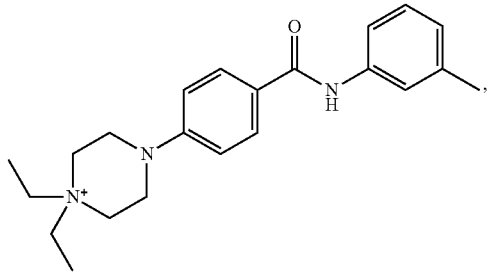

3d

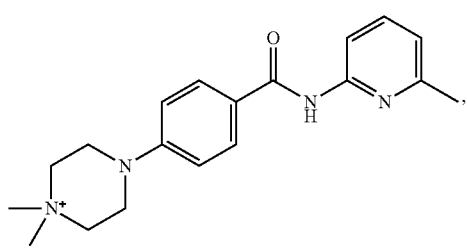

3e

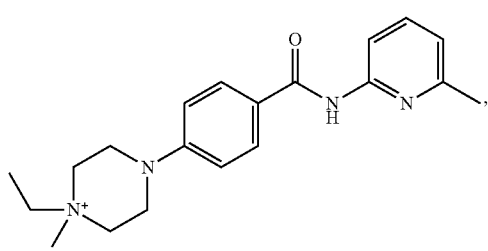

3f

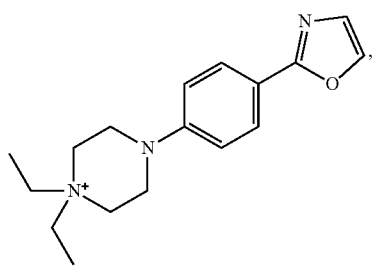

3g

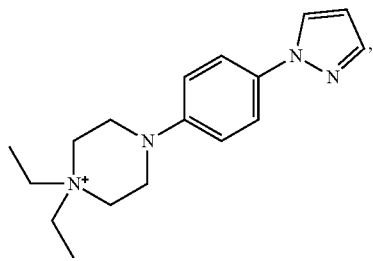

3h

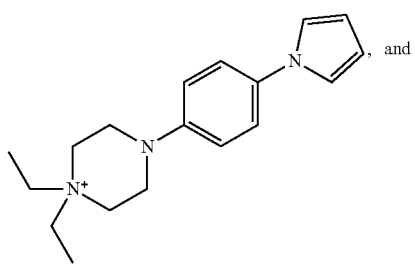

3i, and

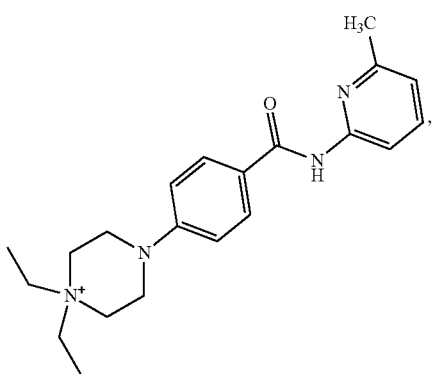

3j or a salt thereof.

In some embodiments of this aspect of the disclosure, the salt of the para-substituted 1,1-dialkyl-4-phenylpiperazin-1-ium can be an iodide.

Another aspect of the disclosure encompasses embodiments of a method of modulating the electrophysiological activity of a nicotinic acetylcholine receptor (nAChR) of an animal cell, the method comprising contacting an animal cell with a para-substituted 1,1-dialkyl-4-phenylpiperazin-1-ium having the formula:

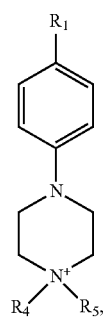

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the compound can be selected from the group consisting of the formulae:

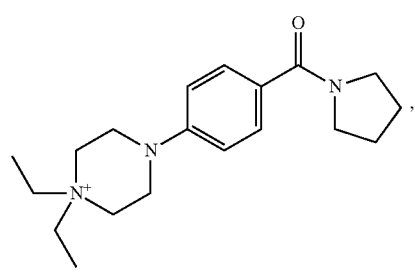

3a

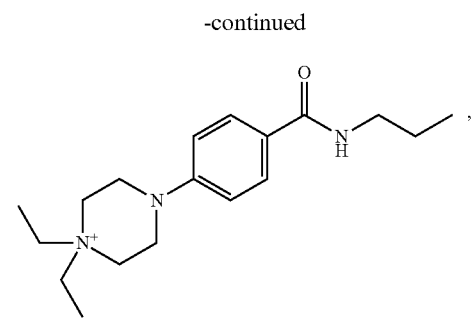

3b

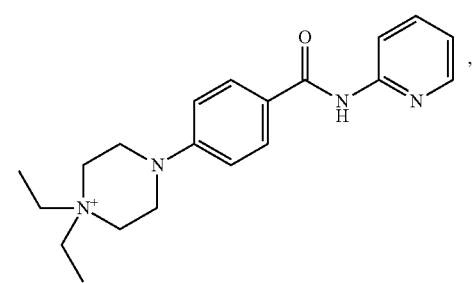

3c

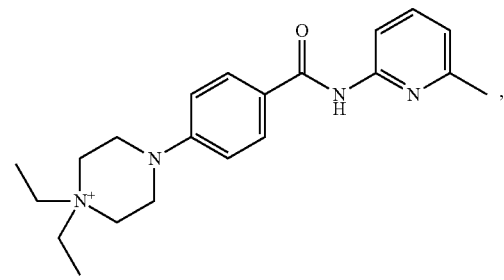

3d

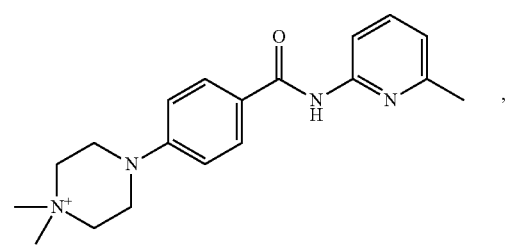

3e

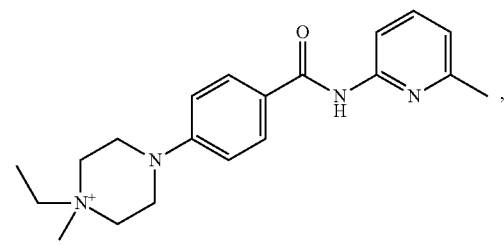

3f

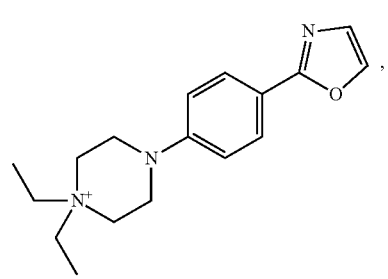

3g

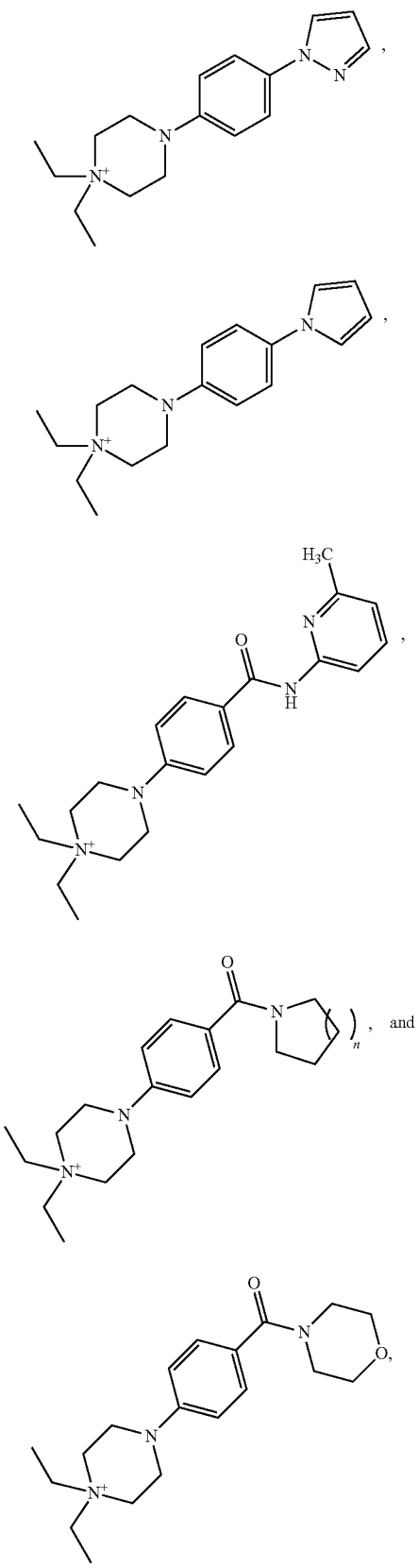

or a salt thereof.

In some embodiments of this aspect of the disclosure, the salt of the para-substituted 1,1-dialkyl-4-phenylpiperazin-1-ium can be an iodide.

In some embodiments of this aspect of the disclosure, the nAChR is an α9, an α9α10, or an α7 nAChR.

Yet another aspect of the disclosure encompasses embodiments of a method of modulating inflammatory signaling by modulating the electrophysiological activity of a nicotinic acetylcholine receptor (nAChR) of an animal cell, the method comprising delivering to an animal cell a para-substituted 1,1-dialkyl-4-phenylpiperazin-1-ium having the formula:

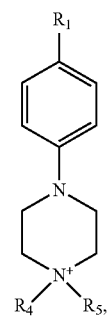

wherein $R_1$ can be a —CO—$R_2$ group, an oxazole, a pyrazole, or a pyrrole; $R_2$ can be a pyrrolidine group or an —NH—$R_3$ group; $R_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and $R_4$ and $R_5$ are each independently a methyl group or an ethyl group, or a salt thereof.

In some embodiments of this aspect of the disclosure, the compound can be selected from the group consisting of the formulae:

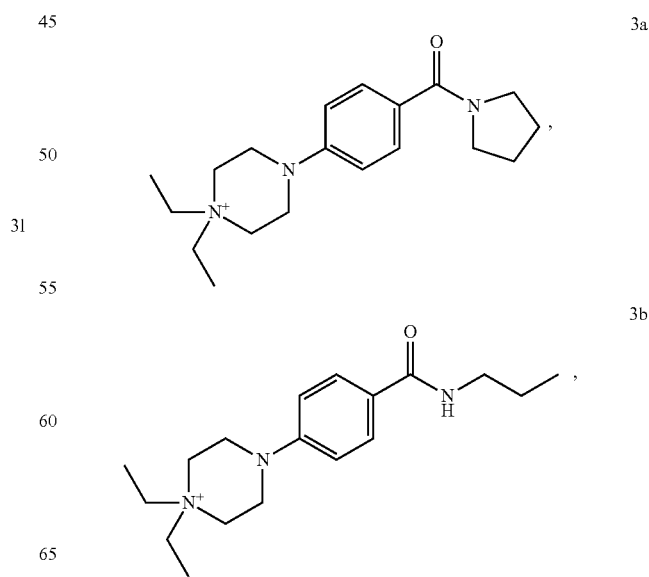

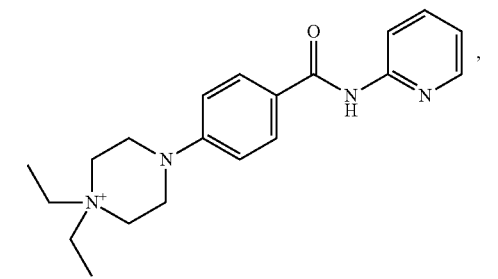 3c

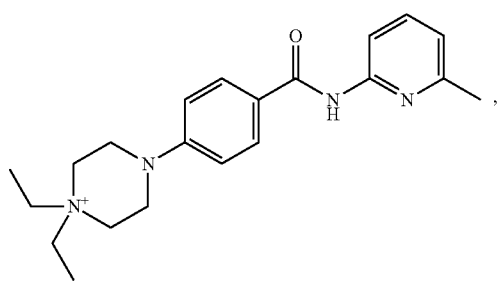 3d

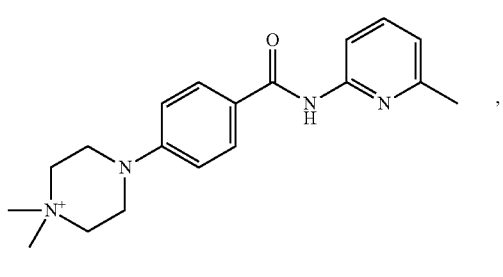 3e

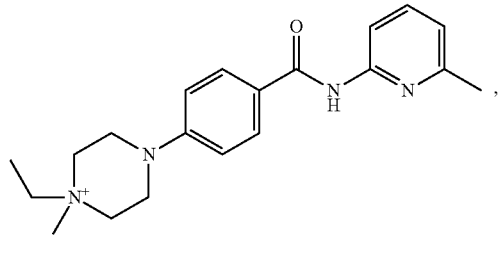 3f

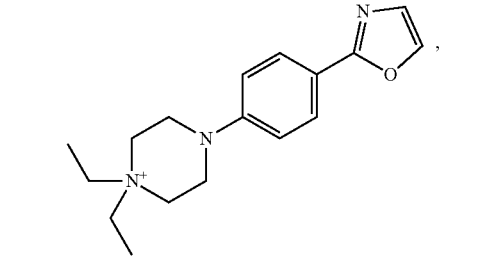 3g

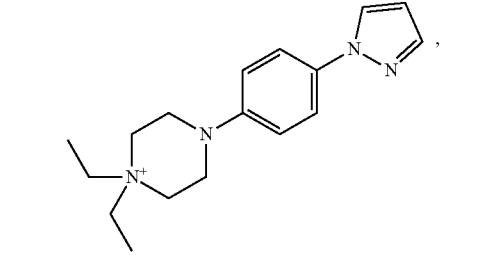 3h

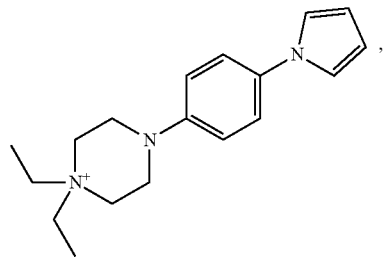 3i

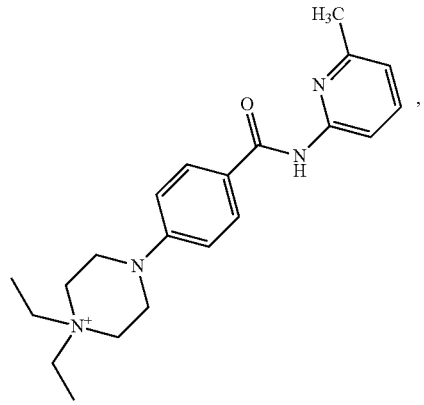 3j

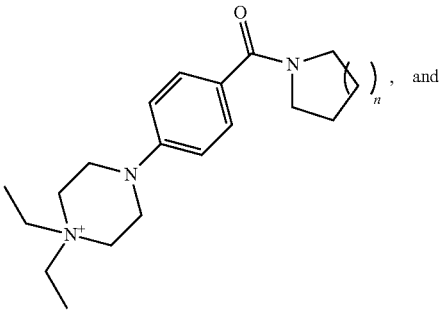 3k

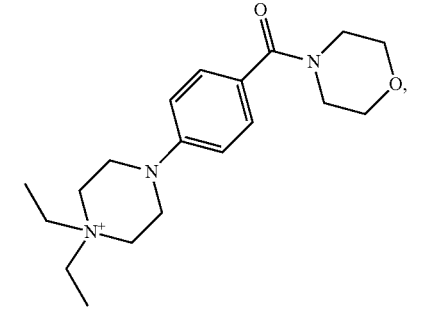 3l or a salt thereof.

In some embodiments of this aspect of the disclosure, the salt of the para-substituted 1,1-dialkyl-4-phenylpiperazin-1-ium can be an iodide.

In some embodiments of this aspect of the disclosure, the nAChR is an α9, an α9α10, or an α7 nAChR.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

General Procedures: All reagents for chemical synthesis were of reagent quality or were purified before use. Organic solvents were of analytical grade or were purified by standard procedures. Reactions were monitored on EMD Millipore 0.25 mm silica gel TLC plates (with fluorescence UV indicator F254) using the solvent system specified in the corresponding experimental protocol. TLC plates were visualized under UV illumination at 254 nm. Column chromatography was performed with silica gel 60 (230-400 mesh). Melting points were obtained on a MFB-595010 M Gallenkamp apparatus equipped with a digital thermometer and are uncorrected. Proton ($^1$H) and carbon ($^{13}$C) NMR spectra were recorded on a Bruker spectrometer (400 MHz and 600 MHz for $^1$H and 101 MHz and 151 MHz for $^{13}$C) using CDCl$_3$ or Methanol-d$_4$ and DMSO-d$_6$ as solvent. Chemical shifts (δ scale) are given in parts per million (ppm) relative to the peak of residual solvent. Processing of the spectra was performed using MestReNova 14.1.1. $^1$H and $^{13}$C-NMR and mass spectra for new compounds are provided in the supporting information section. Reactions were conducted in flame-dried glassware under argon when anhydrous conditions were required. In those cases, anhydrous solvents were used in the reactions. Compound purity was more than 95% as determined by $^1$H NMR analyses. The syntheses of compounds 1 and 2 have been described (Papke et al., (2022) *ACS Chem. Neurosci.* 13: 624-637).

Example 2

Synthesis of 4-bromophenyl)(pyrrolidin-1-yl)methanone (6a): An oven-dried round bottom flask was flushed with Ar and charged with pyrrolidine (5a) (1.5 mL, 18.24 mmol, 2.0 equiv). Lithium bis(trimethylsilyl)amide (LiHMDS) 1.0 M in THF, 3.0 eq (27.3 mL, 27.4 mmol,) was added with vigorous stirring at room temperature, followed by dropwise addition of ethyl 4-bromobenzoate (4) (neat, 1.46 mL, 9.12 mmol 1.0 equiv) and the reaction mixture was stirred at room temperature. After completion of the reaction (monitored by TLC), the reaction mixture was quenched with aqueous ammonium chloride (1.0 M, 10 mL), then diluted with dichloromethane (30 mL), and the resulting the organic layer was washed with water (1×30 mL), brine (1×30 mL), then dried and concentrated and dried under vacuum. 2.10 g, 8.22 mmol, of (4-bromophenyl)(pyrrolidin-1-yl)methanone (6a) was obtained as a brown oil. Yield: 90%; TLC Rf=0.23 in n-hexane:ethylacetate (6:4). $^1$H NMR (400 MHz, Chloroform-d) δ 7.37 (dd, J=2.1, 8.5 Hz, 2H), 7.31-7.17 (m, 2H), 3.45 (dt, J=3.7, 7.2 Hz, 2H), 3.25 (dt, J=3.8, 7.6 Hz, 2H), 1.75 (m, 4H). $^{13}$C NMR (101 MHz, Chloroform-d) δ 168.15, 135.55, 131.05, 128.50, 123.70, 49.22, 45.94, 26.02, 24.01. HRMS (ESI) exact mass calculated for C$_{11}$H$_{12}$BrNO [M+H]$^+$: 254.0175. Found 254.0188.

Example 3

Synthesis of 4-Bromo-N-propylbenzamide (6b): This compound was prepared from ethyl 4-bromobenzoate 4 (1.46 mL, 9.12 mmol 1.0 equiv) and n-propylamine 5b (1.5 mL, 18 mmol, 2.0 equiv) using the procedure described for 6a to afford the desired product 6b obtained as a shiny white solid (2.11 g, 8.72 mmol, 96%). m.p: 78.1-79.5° C., TLC Rf=0.33 in n-hexane:ethyl acetate (6:4). $^1$H NMR (400 MHz, Chloroform-d) δ 7.69-7.60 (m, 2H), 7.58-7.50 (m, 2H), 6.44 (s, 1H), 3.39 (ddd, J=5.9, 7.2, 8.0 Hz, 2H), 1.63 (h, J=7.4 Hz, 2H), 0.98 (t, J=7.4 Hz, 3H). $^{13}$C NMR (101 MHz, Chloroform-d) δ 166.60, 133.60, 131.64, 128.46, 125.85, 41.81, 22.80, 11.38.

Example 4

Synthesis of 4-Bromo-N-(pyridin-2-yl)benzamide (6c): This compound was prepared from ethyl 4-bromobenzoate 4 1.46 mL, 9.12 mmol 1.0 equiv) and 2-aminopyridine 5c (1.71g, 18.2 mmol, 2.0 equiv) using the procedure described for 6a to afford the desired product 6c as a light beige solid (2.39 g, 8.62 mmol, 95% yield). m.p: 123.2-125.7° C., TLC Rf=0.26 in n-hexane:ethyl acetate (7:3). $^1$H NMR (600 MHz, Chloroform-d) δ 8.88 (s, 1H), 8.36 (d, J=8.3 Hz, 1H), 8.22 (t, J=4.1 Hz, 1H), 7.82-7.74 (m, 3H), 7.62 (d, J=8.1 Hz, 2H), 7.07 (dd, J=4.9, 7.3 Hz, 1H). $^{13}$C NMR (151 MHz, Chloroform-d) δ 164.83, 151.39, 147.86, 138.54, 133.11, 132.05, 128.83, 127.05, 120.10, 114.28.

Example 5

Synthesis of 4-Bromo-N-(m-tolyl)benzamide (6d): This compound was prepared from ethyl 4-bromobenzoate (4) (1.46 mL, 9.12 mmol 1.0 equid) and m-toluidine 5d (1.97 mL, 18.2 mmol, 2.0 equiv) using the procedure described for 6a to afford the desired product 6d as a shiny beige solid (2.52 g, 8.87 mmol, 95% yield) m.p: 133.1-134.6° C., TLC Rf=0.35 in n-hexane:ethyl acetate (7:3). $^1$H NMR (400 MHz, Chloroform-d) δ 8.05 (s, 1H), 7.73-7.65 (m, 2H), 7.54 (dd, J=1.6, 8.5 Hz, 2H), 7.46 (d, J=1.9 Hz, 1H), 7.40 (dd, J=2.1, 8.0 Hz, 1H), 7.22 (t, J=7.8 Hz, 1H), 6.97 (m, 1H), 2.33 (s, 3H). $^{13}$C NMR (101 MHz, Chloroform-d) δ 164.93, 138.98, 137.53, 133.76, 131.85, 128.85, 128.63, 126.41, 125.60, 121.07, 117.51, 21.44.

Example 6

Synthesis of 4-Bromo-N-(6-methylpyridin-2-yl)benzamide (6e): This compound was prepared from ethyl 4-bromobenzoate (4) (1.46 mL, 9.12 mmol 1.0 equiv) and 6-methylpyridin-2-amine 5e (1.97g, 18.2 mmol, 2.0 eq) using the procedure described for 6a to afford the desired product 6e as a pale white solid (2.43 g, 8.35 mmol, 92% yield), m.p: 73.7-74.3° C., TLC Rf=0.31 in n-hexane:ethyl acetate (6:4). $^1$H NMR (600 MHz, Methanol-$d_4$) δ 8.02 (dd, J=4.6, 8.5 Hz, 1H), 7.88 (ddd, J=1.7, 6.4, 10.3 Hz, 2H), 7.75-7.65 (m, 3H), 7.07-7.01 (m, 1H), 2.49 (s, 3H, CH$_3$). $^{13}$C NMR (151 MHz, Methanol-$d_4$) δ 157.01, 150.89, 138.51, 133.24, 131.55, 129.11, 126.38, 119.33, 111.68, 111.66, 22.59.

Example 7

Synthesis of 4-(4-Ethylpiperazin-1-yl)phenyl)(pyrrolidin-1-yl)methanone (7a): In a round-bottom flask with a continuous supply of nitrogen, (4-bromophenyl)(pyrrolidin-1-yl)methanone (6a) (0.89 g, 3.52 mmol), Pd$_2$(dba)$_3$ (0.32 g, 0.352 mmol (10 mol %)), (2,2'-bis(diphenylphosphino)-1,1'-binaphthyl ligand (BINAP) (0.438 g, 0.704 mmol, 20 mol %), 1-ethylpiperazine (1.78 mL, 14.08 mmol), and Cs$_2$CO$_3$ (2.94 g, 7.04 mmol) were dissolved in 1 mL of dioxane and 3 mL of dry THF and stirred at 90° C. for 8 h. The reaction mixture was evaporated, and the residue was dissolved in dichloromethane, then filtered over celite. The filtrate was extracted with water (30 mL) to remove excess of ethyl piperazine. The DCM layer was concentrated, and the product was purified by column chromatography on silica gel, eluting with ethyl acetate. The fractions containing the desired product were combined, evaporated, and dried. Compound 7a was obtained as a pale brown oil (0.65 g, 2.3 mmol, yield: 64% yield). TLC Rf=0.24 in 95% ethyl acetate in n-hexane. $^1$H NMR (400 MHz, Chloroform-d) δ 7.48 (d, J=8.8 Hz, 2H), 6.87 (d, J=8.8 Hz, 2H), 3.61 (t, J=7.0 Hz, 2H), 3.50 (t, J=6.4 Hz, 2H), 3.32-3.20 (m, 4H), 2.58 (m, 4H), 2.46 (q, J=7.2 Hz, 2H), 2.00-1.77 (m, 4H), 1.12 (t, J=7.2 Hz, 3H). $^{13}$C NMR (101 MHz, Chloroform-d) δ 169.55, 152.17, 128.87, 127.14, 114.21, 52.59, 52.29, 49.75, 48.16, 46.27, 26.49, 24.39, 11.95. HRMS (ESI) exact mass calculated for C$_{17}$H$_{25}$N$_3$O [M+H]$^+$: 288.2070, Found 288.2079 and [M+Na]$^+$: 310.1890, Found 310.1884.

Example 8

Synthesis of 4-(4-Ethylpiperazin-1-yl)-N-propylbenzamide (7b): Prepared from 6b (0.852 g, 3.52 mmol) and N-ethyl piperazine (1.78 mL, 14.1 mmol) in dioxane 1 mL and toluene 3 mL using the procedure and conditions described for 7a to afford the desired product 7b as a pale white solid (0.90 g, 3.3 mmol, 64% yield). m.p: 126.4-128.8° C. TLC Rf=0.28 in 95:5 ethyl acetate/n-hexane. $^1$H NMR (400 MHz, Chloroform-d) δ 7.67 (d, J=8.9 Hz, 2H), 6.88 (d, J=8.9 Hz, 2H), 6.02 (s, 1H), 3.39 (m, 2H), 3.34-3.27 (m, 4H), 2.64-2.56 (m, 4H), 2.48 (q, J=7.2 Hz, 2H), 1.68-1.54 (m, 2H), 1.13 (t, J=7.2 Hz, 3H), 0.96 (t, J=7.4 Hz, 3H). $^{13}$C NMR (101 MHz, Chloroform-d) δ 167.35, 153.42, 128.40, 124.85, 114.50, 52.77, 52.56, 48.12, 41.82, 23.27, 12.15, 11.68. HRMS (ESI) exact mass calculated for C$_{16}$H$_{25}$N$_3$O [M+H]$^+$: 276.2070, Found 276.2078 and [M+Na]$^+$: 298.1890, Found 298.1887.

Example 9

Synthesis of 4-(4-Ethylpiperazin-1-yl)-N-(pyridin-2-yl)benzamide (7c): Prepared from 6c (0.975 g, 3.52 mmol) and N-ethyl piperazine (1.78 mL, 14.1 mmol) in 4 mL of dioxane and toluene (1:3) using the procedure and conditions described for 7a to afford the desired product 7c as a pale white solid (0.73 g, 2.4 mmol, 67% yield). m.p: 124.3-126° C. TLC Rf=0.28 in 95% ethyl acetate in n-hexane. $^1$H NMR (400 MHz, Chloroform-d) δ 8.72 (s, 1H), 8.37 (d, J=8.4 Hz, 1H), 8.22 (d, J=4.9 Hz, 1H), 7.91-7.76 (m, 2H), 7.71 (td, J=1.8, 7.9 Hz, 1H), 7.00 (dd, J=5.0, 7.3 Hz, 1H), 6.90 (d, J=8.6 Hz, 2H), 3.34 (t, J=5.1 Hz, 4H), 2.58 (t, J=5.0 Hz, 4H), 2.46 (q, J=7.2 Hz, 2H), 1.12 (t, J=7.2 Hz, 3H). $^{13}$C NMR (101 MHz, Chloroform-d) δ 165.26, 153.65, 151.94, 147.70, 138.28, 128.80, 123.25, 119.38, 114.06, 113.94.43, 52.26, 47.46, 11.90. HRMS (ESI) exact mass calculated for C$_{18}$H$_{22}$N$_4$O [M+H]$^+$: 311.1866, Found 311.1880 and [M+Na]$^+$: 333.168, Found 333.1691.

Example 10

Synthesis of 4-(4-Ethylpiperazin-1-yl)-N-(m-tolyl)benzamide (7d): This compound was prepared from 6d (1.02 g, 3.52 mmol) and N-ethyl piperazine (1.78 mL, 14.1 mmol) in dioxane 1 mL and toluene 3 mL using the procedure and conditions described for 7a to afford the desired product 7d as a pale-yellow solid (0.92 g, 2.8 mmol, 81% yield). m.p: 154-156.6° C. TLC Rf=0.32 in ethyl acetate:Methanol (9:1). $^1$H NMR (400 MHz, Chloroform-d) δ 7.82-7.76 (m, 2H), 7.74 (s, 1H), 7.51 (d, J=2.1 Hz, 1H), 7.40 (dd, J=2.2, 7.9 Hz, 1H), 7.23 (t, J=7.8 Hz, 1H), 6.97-6.89 (m, 3H), 3.38-3.31 (m, 4H), 2.61 (t, J=5.1 Hz, 4H), 2.49 (d, J=7.2 Hz, 2H), 2.36 (s, 3H), 1.14 (t, J=7.2 Hz, 3H). $^{13}$C NMR (101 MHz, Chloroform-d) δ 165.22, 153.48, 138.88, 138.23, 128.79, 128.48, 124.85, 124.32, 120.67, 117.07, 114.17, 52.53, 52.33, 47.72, 21.52, 11.98.

Example 11

Synthesis of 4-(4-methylpiperazin-1-yl)-N-(6-methylpyridin-2-yl)benzamide (7e): This compound was prepared from 6e (1.02 g, 3.52 mmol) and N-methyl piperazine (1.56 mL, 14.1 mmol) in 3 mL of dioxane and toluene (1:2) using the procedure and conditions described for 7a to afford the desired product 7e as an off-white solid (0.89 g, 2.9 mmol, 82% yield). m.p: 128.3-131.1° C. TLC Rf=0.29 in ethyl acetate:Methanol (9:1). $^1$H NMR (400 MHz, Methanol-$d_4$) δ 8.04 (d, J=8.3 Hz, 1H), 7.95-7.86 (m, 2H), 7.72 (t, J=7.9 Hz, 1H), 7.05 (dd, J=8.1, 10.4 Hz, 3H), 3.44-3.36 (m, 4H), 2.67-2.59 (m, 4H), 2.50 (s, 3H), 2.38 (s, 3H). $^{13}$C NMR (101 MHz, Methanol-$d_4$) δ 168.00, 158.34, 155.37, 152.77, 140.08, 130.31, 124.61, 120.39, 115.38, 113.01, 55.85, 48.36, 46.22, 24.02.

Example 12

Synthesis of 1,1-diethyl-4-(4-(pyrrolidine-1-carbonyl)phenyl)piperazin-1-ium iodide (3a): In a sealed vial, the coupled compound 7a (0.22 g, 0.76 mmol, 1 eq) was dissolved in 0.5 mL dry THF and iodoethane (0.62 mL, 7.7 mmol, 10 eq.) was added; the resulting mixture was stirred at 25° C. for 24 hours until complete consumption of the starting material (TLC in ethylacetate:methanol (7:3). Upon completion of the reaction, hexane was added to the reaction mixture to remove excess iodoethane. The hexane solution was pipetted from the mixture leaving behind a residue that was dissolved in DCM (2 mL). Addition of pentane (8 mL) lead to formation of a precipitate that was allowed to settle, and the resulting supernatant was carefully removed by pipetting. Solvent was further removed from the resulting solid under high vacuum to afford 3a (0.20 g, 0.45 mmol, 59%) as a pale yellow hygroscopic solid that was stored under argon. TLC Rf=0.33 in ethyl acetate: methanol (7:3). $^1$H NMR (400 MHz, Chloroform-d) δ 7.46 (d, J=8.5 Hz, 2H), 6.95 (d, J=8.5 Hz, 2H), 3.60 (m, 16H), 1.97-1.91 (m, 2H), 1.90-1.84 (m, 2H), 1.39 (t, J=7.1 Hz, 6H). $^{13}$C NMR (101 MHz, Chloroform-d) δ 169.11, 149.87, 129.31, 128.83, 115.31, 77.32, 77.00, 76.68, 57.48, 53.71, 49.74, 46.33, 42.28, 26.45, 24.40, 7.75. HRMS (ESI) exact mass calculated for $C_{19}H_{30}N_3O^+$ [M]$^+$: 316.2389. Found 316.2393.

Example 13

Synthesis of 1,1-diethyl-4-(4-(propylcarbamoyl)phenyl)piperazin-1-ium iodide (3b): This compound was prepared from 7b (0.35 g, 1.27 mmol) and iodoethane (1.02 mL, 12.1 mmol) using the procedure and conditions described for 3a to afford the desired product 3b. The product was precipitated from ethyl acetate and obtained as a white solid (0.390 g, 0.904 mmol, 71% yield). m.p: 231-233.8° C. TLC Rf=0.29 in ethyl acetate: Methanol (7:3). $^1$H NMR (400 MHz, Methanol-d$_4$) δ 7.83-7.74 (m, 2H), 7.11-7.02 (m, 2H), 3.65 (s, 8H), 3.56 (q, J=7.3 Hz, 4H), 1.62 (h, J=7.3 Hz, 2H), 1.37 (t, J=7.3 Hz, 6H), 0.96 (t, J=7.4 Hz, 3H). $^{13}$C NMR (101 MHz, Methanol-d$_4$) δ 169.83, 153.22, 129.85, 127.17, 115.97, 58.50, 54.24, 42.89, 42.78, 23.91, 11.86, 7.41. HRMS (ESI) exact mass calculated for $C_{18}H_{30}N_3O^+$ [M]$^+$: 304.2383. Found 304.2398.

Example 14

Synthesis of 1,1-diethyl-4-(4-(pyridin-2-ylcarbamoyl)phenyl)piperazin-1-ium iodide (3c). This compound was prepared from 7c (0.25 g, 0.80 mmol) and iodoethane (0.65 mL, 8.05 mmol) using the procedure and conditions described for 3a to afford the desired product 3c. The product was obtained as a pink-white solid after precipitation from ethyl acetate (0.27 g, 0.57 mmol, 72% yield). m.p: 226.1-227.9° C., TLC Rf=0.23 in ethyl acetate:Methanol (7:3). $^1$H NMR (400 MHz, Methanol-d$_4$) δ 8.39-8.32 (m, 1H), 8.22 (d, J=8.4 Hz, 1H), 8.02-7.93 (m, 2H), 7.84 (m, 1H), 7.21-7.12 (m, 3H), 3.72 (d, J=5.7 Hz, 4H), 3.70-3.63 (m, 4H), 3.59 (q, J=7.2 Hz, 4H), 1.40 (t, J=7.3 Hz, 6H). $^{13}$C NMR (101 MHz, Methanol-d$_4$) δ 167.67, 153.51, 153.12, 148.84, 139.42, 130.20, 126.02, 120.91, 116.05, 115.57, 58.14, 53.97, 42.34, 7.13. HRMS (ESI) exact mass calculated for $C_{20}H_{27}N_4O^+$ [M]$^+$: 339.2179, Found 339.2180.

Example 15

Synthesis of 1,1-diethyl-4-(4-(m-tolylcarbamoyl)phenyl)piperazin-1-ium iodide (3d): This compound was prepared from 7d (0.35 g, 1.08 mmol) and iodoethane (0.87 mL, 11 mmol) using the procedure and conditions described for 3a to afford the product as a beige-white solid after precipitation from ethyl acetate (0.38 g, 0.79 mmol, 73% yield). m.p: 201.1-203.3° C. TLC Rf=0.25 in ethyl acetate:Methanol (7:3). $^1$H NMR (600 MHz, DMSO-d$_6$) δ 9.90 (s, 1H), 7.96-7.91 (m, 2H), 7.60 (d, J=1.8 Hz, 1H), 7.58-7.54 (m, 1H), 7.21 (t, J=7.8 Hz, 1H), 7.13-7.08 (m, 2H), 6.89 (d, J=7.5 Hz, 1H), 3.65 (t, J=5.2 Hz, 4H), 3.57 (t, J=5.2 Hz, 4H), 3.50 (q, J=7.2 Hz, 4H), 2.30 (s, 3H), 1.23 (t, J=7.2 Hz, 6H). $^{13}$C NMR (101 MHz, DMSO-d$_6$) δ 164.70, 151.59, 139.31, 137.61, 129.04, 128.35, 124.92, 123.99, 120.83, 117.47, 113.87, 56.16, 51.88, 40.58, 40.15, 21.23, 6.76. HRMS (ESI) exact mass calculated for $C_{22}H_{30}N_3O^+$ [M]$^+$: 352.2383. Found 352.2400.

Example 16

Synthesis of 1,1-dimethyl-4-(4-((6-methylpyridin-2-yl)carbamoyl)phenyl)piperazin-1-ium iodide (3e). This product was prepared from 7e (0.35 g, 1.1 mmol) and iodomethane (0.70 mL, 11 mmol) using the procedure and conditions described for 3a with a reaction time of 2 h, affording product as a pale yellow solid after precipitation from ethyl acetate (0.40 g, 0.88 mmol, 78% yield). m.p: 135.5-137.7° C. TLC Rf=0.27 in ethyl acetate:Methanol (7:3). $^1$H NMR (400 MHz, Methanol-d$_4$) δ 8.02 (d, J=8.2 Hz, 1H), 7.98-7.89 (m, 2H), 7.72 (t, J=7.9 Hz, 1H), 7.19-7.11 (m, 2H), 7.04 (d, J=7.5 Hz, 1H), 3.72 (dd, J=6.0, 17.3 Hz, 8H), 3.34 (s, 6H), 2.49 (s, 3H). $^{13}$C NMR (101 MHz, Methanol-d$_4$) δ 167.73, 158.41, 153.76, 152.63, 140.13, 131.81, 130.43, 126.49, 120.57, 116.14, 113.08, 62.50, 52.00, 43.25, 24.03. HRMS (ESI) exact mass calculated for $C_{19}H_{25}N_4O^+$ [M]$^+$: 325.2023. Found 352.2037.

Example 17

Synthesis of 1-ethyl-1-methyl-4-(4-((6-methylpyridin-2-yl)carbamoyl)phenyl)piperazin-1-ium iodide (3f): This compound was prepared from 7e (0.27 g, 0.87 mmol) and iodoethane (0.70 mL, 8.7 mmol) using the procedure and conditions described for 3a to afford the product 3f as a pink-white solid after precipitation from ethyl acetate (0.29 g, 0.62 mmol, 72% yield). m.p: 207.2-209.4° C. TLC Rf=0.26 in ethyl acetate:Methanol (7:3). $^1$H NMR (400 MHz, DMSO-d$_6$) δ 10.42 (s, 1H), 8.07-7.96 (m, 3H), 7.70 (t, J=7.9 Hz, 1H), 7.13-7.05 (m, 2H), 7.00 (d, J=7.4 Hz, 1H), 3.80-3.48 (m, 10H), 3.12 (s, 3H), 2.45 (s, 3H), 1.30 (t, J=7.2 Hz, 3H). $^{13}$C NMR (101 MHz, Methanol-d$_4$) δ 167.65, 158.33, 153.71, 152.56, 140.03, 130.33, 126.29, 120.48, 115.99, 112.99, 60.97, 60.45, 46.67, 42.92, 23.98, 7.79. HRMS (ESI) exact mass calculated for $C_{20}H_{27}N_4O^+$ [M]$^+$: 339.2179. Found 339.2193.

Example 18

Synthesis of 2-(4-(4-ethylpiperazin-1-yl)phenyl)oxazole (9a): In a sealed vial purged with nitrogen, 2-(4-iodophenyl)oxazole (8a) (0.85g, 3.1 mmol, 1 eq.), Pd$_2$(dba)$_3$ (0.28 g, 0.31 mmol (10 mol %)), (2,2'-bis(diphenylphosphino)-1,1'-binaphthyl ligand (BINAP) (0.586 g, 0.94 mmol, 30 mol %), 1-ethylpiperazine (1.6 mL, 2.5 mmol, 4 eq.), and Cs$_2$CO$_3$ (2.04 g, 6.27 mmol, 2 eq.) were dissolved in dioxane (2 mL) and toluene (2 mL) and stirred at 120° C. for 48 h. The reaction mixture was evaporated, and the residue was dissolved in dichloromethane, then filtered over celite. The filtrate was extracted with water (30 mL) to remove excess ethyl piperazine. The DCM layer was concentrated, and the product was purified by column chromatography on silica gel, eluting with ethyl acetate. The fractions containing the desired product were combined, evaporated, and dried under high vacuum. 9a (0.50 g, 1.9 mmol, 62%) was obtained as a pale white solid. m.p: 120.2-122.8° C. TLC Rf=0.28 in ethyl acetate:Methanol (9:1). $^1$H NMR (400 MHz, Chloroform-d) δ 7.96-7.86 (m, 2H), 7.63 (s, 1H), 7.16 (s, 1H), 6.98-6.90 (m, 2H), 3.38-3.29 (m, 4H), 2.63 (t, J=5.0 Hz, 4H), 2.50 (q, J=7.2 Hz, 2H), 1.15 (t, J=7.2 Hz, 3H). $^{13}$C NMR (101 MHz, Chloroform-d) δ 162.57, 152.55, 137.81, 128.25, 127.76, 118.38, 115.06, 52.75, 52.54, 48.13, 12.08. HRMS (ESI) exact mass calculated for $C_{15}H_{19}N_3O$ $[M+H]^+$: 258.1601. Found 258.1606.

Example 19

Synthesis of 1-(4-(1H-pyrazol-1-yl)phenyl)-4-ethylpiperazine (9b): This compound was prepared from 1-(4-iodophenyl)-1H-pyrazole 8b (0.70 g, 2.6 mmol) and ethyl piperazine (1.3 mL, 10 mmol) using the procedure and conditions described for 9a to afford the desired product 9b (0.38 g, 1.5 mmol, 57% yield) as a pale yellow solid. m.p: 116.8-119.1° C. TLC Rf=0.27 in ethyl acetate:Methanol (9:1). $^1$H NMR (400 MHz, Chloroform-d) δ 7.80 (d, J=2.4 Hz, 1H), 7.66 (d, J=1.8 Hz, 1H), 7.54 (d, J=9.0 Hz, 2H), 6.97 (d, J=9.0 Hz, 2H), 6.40 (s, 1H), 3.31-3.14 (m, 4H), 2.63 (dd, J=3.9, 6.3 Hz, 4H), 2.48 (q, J=7.2 Hz, 2H), 1.13 (t, J=7.2 Hz, 3H). $^{13}$C NMR (101 MHz, Methanol-$d_4$) δ 151.63, 141.51, 134.89, 129.08, 121.91, 117.77, 108.21, 53.82, 53.42, 49.87, 11.88. HRMS (ESI) exact mass calculated for $C_{15}H_{20}N_4$ $[M+H]^+$: 257.1761. Found 257.1771.

Example 20

Synthesis of 1-(4-(1H-pyrrol-1-yl)phenyl)-4-ethylpiperazine (9c): This compound was prepared from 1-(4-iodophenyl)-1H-pyrrole 8c (0.70 g, 2.6 mmol) and ethyl piperazine (1.32 mL, 10.4 mmol) using the procedure and conditions described for 9a to afford the desired product 9c 5 (0.35 g, 1.4 mmol, 53% yield) as a pale white solid. m.p: 115.6-117.2° C. TLC Rf=0.30 in ethyl acetate:Methanol (9:1). $^1$H NMR (400 MHz, Methanol-$d_4$) δ 7.32 (d, J=9.0 Hz, 2H), 7.07-6.99 (m, 4H), 6.22 (t, J=2.2 Hz, 2H), 3.25-3.16 (m, 4H), 2.70-2.60 (m, 4H), 2.51 (q, J=7.2 Hz, 2H), 1.15 (t, J=7.3 Hz, 3H). $^{13}$C NMR (101 MHz, Chloroform-d) δ 143.34, 130.51, 121.82, 119.57, 116.80, 109.66, 52.72, 52.35, 49.25, 12.08. HRMS (ESI) exact mass calculated for $C_{16}H_{21}N_3$ $[M+H]^+$: 256.1808. Found 256.1815.

Example 21

Synthesis of 1,1-diethyl-4-(4-(oxazol-2-yl)phenyl)piperazin-1-ium iodide (3g): In a sealed vial, the coupled compound 9a (0.30 g, 1.2 mmol) was dissolved in dry THF (0.5 mL), iodoethane (0.93 mL, 11.65 mmol) was added, and the resulting mixture was stirred at 25° C. for 2 days until complete consumption of the starting material (TLC in ethylacetate: methanol (7:3). Upon completion, hexane was added to the reaction mixture followed by filtration. 3g was obtained as a pale white solid after precipitation from ethyl acetate (0.312 g, 0.755 mmol, 65%; m.p: 222.2-224° C. TLC Rf=0.29 in ethyl acetate:methanol (7:3). $^1$H NMR (500 MHz, Methanol-$d_4$) δ 7.97-7.91 (m, 3H), 7.26-7.23 (m, 1H), 7.19-7.12 (m, 2H), 3.68 (s, 8H), 3.59 (q, J=7.1 Hz, 4H), 1.39 (t, J=7.2 Hz, 6H). $^{13}$C NMR (101 MHz, Methanol-$d_4$) δ 163.77, 152.62, 140.23, 128.79, 128.72, 120.14, 116.73, 58.51, 54.30, 42.92, 7.52. HRMS (ESI) exact mass calculated for $C_{17}H_{24}N_3O^+$ $[M]^+$: 286.1914. Found 286.1926.

Example 22

Synthesis of 4-(4-(1H-pyrazol-1-yl)phenyl)-1,1-diethylpiperazin-1-ium iodide (3h): This compound was prepared from 9b (0.25 g, 0.98 mmol) and iodoethane (0.78 mL, 9.8 mmol) using the procedure and conditions described for 3g to afford the product as a light beige solid after precipitation from ethyl acetate (0.193 g, 0.468 mmol, 48% yield). m.p: 217.4-219.1° C. TLC Rf=0.27 in ethyl acetate:Methanol (7:3). $^1$H NMR (400 MHz, Methanol-$d_4$) δ 8.11 (d, J=2.5 Hz, 1H), 7.69 (d, J=1.8 Hz, 1H), 7.64 (d, J=9.0 Hz, 2H), 7.16 (d, J=9.1 Hz, 2H), 6.50 (s, 1H), 3.71-3.50 (m, 12H), 1.38 (t, J=7.3 Hz, 6H). $^{13}$C NMR (101 MHz, Methanol-$d_4$) δ 151.63, 141.51, 134.89, 129.08, 121.91, 117.77, 108.21, 58.51, 54.30, 42.92, 7.52. HRMS (ESI) exact mass calculated for $C_{17}H_{25}N_4^+$ $[M]^+$: 285.2074. Found 285.2084.

Example 23

Synthesis of 4-(4-(1H-pyrrol-1-yl)phenyl)-1,1-diethylpiperazin-1-ium iodide (3i). This compound was prepared from 9c (0.25 g, 0.98 mmol) and iodoethane (0.8 mL, 10 mmol) using the procedure and conditions described for 3g to afford the product as a light pink solid after precipitation from ethyl acetate (0.187 g, 0.455 mmol, 46% yield). m.p: 218.3-220° C. TLC Rf=0.31 in ethyl acetate:Methanol (7:3). $^1$H NMR (400 MHz, Methanol-$d_4$) δ 7.40 (d, J=8.9 Hz, 2H), 7.12 (d, J=9.0 Hz, 2H), 7.08 (t, J=2.2 Hz, 2H), 6.24 (t, J=2.2 Hz, 2H), 3.72-3.48 (m, 12H), 1.37 (t, J=7.3 Hz, 6H). $^{13}$C NMR (101 MHz, Methanol-$d_4$) δ 161.49, 148.79, 122.27, 120.15, 118.71, 111.07, 58.78, 54.25, 44.28, 7.36. HRMS (ESI) exact mass calculated for $C_{18}H_{26}N_3^+$ $[M]^+$: 284.2121. Found 284.2124.

Example 24

Synthesis of APA-diEPP, 1,1-diethyl-4-(4-((6-methylpyridin-2-yl)carbamoyl)phenyl)piperazin-1-ium iodide: Amidation of p-bromo ethyl benzoate to form 4-bromo-N-(6-methylpyridin-2-yl)benzamide proceeded in 91% yield at room temperature. The second step is the key step in the synthesis, i.e. the C—N cross-coupling reaction for N-arylation of ethyl piperazine, leading to the formation of 4-(4-ethylpiperazin-1-yl)-N-(6-methylpyridin-2-yl)benzamide. Initially the reaction was performed reported in our previous method (Quadri et al., (2016) *Bioorg. Med. Chem.* 24: 286-293); however, the reaction conditions adversely affected the yield. Therefore, we switched to a Buchwald-Hartwig C—N cross-coupling reaction using a palladium catalyst. After exploring a number of catalysts and conditions, we found the reaction utilizing 10 mol % of tris (dibenzylidene acetone)dipalladium0 ($Pd_2$ (dba)$_3$) in cesium carbonate (2.0 equiv) as a base and BINAP (30 mol %) in 2 mL of dioxane afforded a good yield (60%) of coupled product after purification. The synthesis was achieved after some modifications to a reported protocol (Takamura-Enya et al., (2006) *J. Org. Chem*, 71: 5599-5606). Once obtained, the 4-(4-ethylpiperazin-1-yl)-N-(6-methylpyridin-2-yl)benzamide was then converted into the quaternary ammonium salt by alkylation with ethyliodide in tetrahydrofuran and then purified by recrystallization to afford the 1,1-diethyl-4-(4-((6-methylpyridin-2-yl)carbamoyl)phenyl)piperazin-1-ium iodide (APA-diEPP) in 78% yield.

Accordingly, in a sealed vial, the coupled compound (0.25 g, 0.77 mmol, 1 equiv) was dissolved in dry THF (0.5 mL); after addition of some copper as stabilizer, iodoethane (0.49 mL, 6.16 mmol, 8 equiv) was added, and the resulting mixture was heated at 75° C. until complete consumption of the starting material (TLC in ethyl acetate:methanol (7:3). Upon completion, the mixture was cooled to room temperature. n-hexane:ethyl acetate (6:4) was added to the reaction mixture, filtered to remove excess of iodoethane, and followed by recrystallization with ethyl acetate afforded 0.288 grams of white solid; mp 221-223° C. (color changed to pale brown at 201° C. before melting starts). Yield: 78%; Rf=0.39 in ethyl acetate:methanol (7:3). $^1$H NMR (400 MHz, Methanol-$d_4$) δ 8.01 (d, J=8.3 Hz, $^1$H, ArH), 7.99-7.90 (m, 2H, ArH), 7.75-7.67 (m, 1H, ArH), 7.18-7.09 (m, 2H, ArH), 7.03 (d, J=7.5 Hz, 1H, ArH), 3.75-3.62 (m, 8H, 4×$CH_{2\text{-}Pip}$), 3.58 (q, J=7.3 Hz, 4H, 2×$CH_2$), 2.48 (s, 3H, $CH_3$—Ar), 1.38 (t, J=7.3 Hz, 6H, 2×$CH_3$). $^{13}$C NMR (101 MHz, Methanol-$d_4$): δ 166.3, 156.9, 152.3, 151.1, 138.6, 128.9, 124.8, 119.1, 114.4, 111.6, 57.0, 52.8, 41.2, 22.5, 6.0. HRMS (ESI) exact mass calculated for $C_{21}H_{29}N_4O^+$ $[M]^+$: 353.2336, found 353.2337.

Example 25

Molecular Biology: Plasmid DNAs encoding the human α7 and heteromeric nAChR were obtained from Jon Lindstrom (University of Pennsylvania, Philadelphia, PA). Mouse muscle subunit clones were obtained from Jim Boulter (Salk Institute, La Jolla CA) and Paul Gardner (Dartmouth, Hanover NH). The human resistance-to-cholinesterase 3 (R103) clone was obtained from Millet Treinin (Hebrew University, Jerusalem, Israel) and RNA co-injected with α7 to improve the level and speed of receptor expression without affecting their pharmacological properties. Plasmid DNA encoding the human α10 nAChR was obtained from J. Michael McIntosh. Plasmid DNA encoding the human α9 nAChR and the human receptor-associated protein of the synapse (RAPSYN) with codon optimization for expression in Xenopus laevis were obtained from Katrin Richter. RAPSYN RNA was co-injected with the α9 and α10 to improve expression (Richter et al., (2022) *Front. Cell Neurosci.* 16: 779081). After linearization and purification of the plasmid DNAs, RNAs were prepared using the mMessage mMachine in vitro RNA transcription kit (Ambion, Austin, TX). Frogs were maintained in the Animal Care Service facility of the University of Florida, and all procedures were approved by the University of Florida Institutional Animal Care and Use Committee (approval number 202002669). In brief, the animals were first anesthetized for 15-20 min in 1.5 l frog tank water containing 1 g of MS-222 buffered with sodium bicarbonate. Oocytes were obtained surgically from mature female Xenopus laevis (Nasco, Ft. Atkinson WI, USA) and treated with 1.4 mg/ml type 1 collagenase (Worthington Biochemicals, Freehold NJ, USA) for 2-4 h at rt in Ca2+-free Barth's solution (88 mM NaCl, 1 mM KCl, 2.38 mM NaHCO3, 0.82 mM MgSO4, 15 mM HEPES, and 12 mg/l tetracycline, pH 7.6) to remove the ovarian tissue and the follicular layers. Stage V oocytes were injected with 4-6 ng CHRNA7 RNA and 2-3 ng RIC3 RNA (2:1 ratio) in 50 nl water, or with 12 ng CHRNA9 RNA and 3 ng RAPSN RNA, or along with 12 ng CHRNA10 RNA in 50 nl water. Oocytes were maintained in Barth's solution containing 0.32 mM Ca(NO$_3$)$_2$ and 0.41 mM CaCl$_2$, and recordings were conducted 2-20 days after injection.

Example 26

Electrophysiology: Two-electrode voltage-clamp experiments were conducted using OpusXpress 6000A (Molecular Devices, Union City CA, USA). Both the voltage and current electrodes were filled with 3 M KCl. Oocytes were voltage-clamped at −60 mV at rt. The oocytes were perfused with Ringer's solution (115 mM NaCl, 2.5 mM KCl, 1.8 mM CaCl2, 10 mM HEPES, 1 μM atropine, pH 7.2) at 2 ml/min. To evaluate the effects of experimental compounds, responses were compared to control ACh-evoked responses, defined as the average of two initial applications of 60 μM ACh made before test applications. Drug applications were 12 s in duration followed by 181 s washout periods.

The responses were calculated as both peak-current amplitudes and net charge. Data were collected at 50 Hz, filtered at 20 Hz, and analyzed by Clampfit (Molecular Devices) and Excel (Microsoft, Redmond, WA, United States). Data are expressed as means±SEM from at least five oocytes for each experiment and plotted with Kaleidagraph 4.5.2 (Abelbeck Software, Reading, PA, United States). Each episode of data acquisition was a total of 210 s and included an initial 30 s period used to define the baseline for the drug-evoked responses. After 30 s, drugs were applied, and the following 120 s were defined as the drug response period for analysis. Data reported for α7 are net charge, while peak currents are used for α9 and α9/α10 responses since these receptors do not show the same concentration-dependent desensitization that invalidates peak currents as measurements of α7 concentration-dependent responses (Richter et al., (2022) *Front. Cell Neurosci.* 16: 779081). The values for the curve fits were generated using the Levenberg-Marquardt algorithm to obtain the best Chi-Square fit to the Hill equation using the Kaleidagraph 4.5.2 plotting program. The errors in the tables are the calculated standard errors of the fit parameters based on the goodness of fit.

Example 27

Docking Studies: The reported homology model for α9 for docking studies (Papke et al., (2022) *ACS Chem. Neurosci.* 13: 624-637) was utilized. The dimeric model was used for docking studies using Glide in SP mode (Schrodinger, Inc). The grid employed was sufficiently large as to encompass the orthosteric site of the receptor; the center bounding box, used to define the region that the molecular midpoints can reside in during docking, was set to a cube of 20×20×20 Å. Ligands were prepared with the LigPrep routine, and allowed to be flexible during docking. For each ligand, the top three poses based on Glide score were retained for examination.

We claim:

1. A method of treating a disease or disorder modulated by nicotinic acetylcholine receptor (nAChR) function in a subject, the method comprising administering a pharmaceutical composition comprising
    a para-substituted 1,1-dialkyl-4-phenylpiperazin-1-ium having the formula:

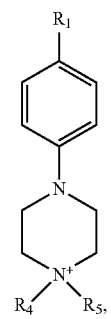

wherein:

R$_1$ is a —CO—R$_2$ group, an oxazole, a pyrazole, or a pyrrole;

R$_2$ is a pyrrolidine group or an —NH—R$_3$ group;

R$_3$ is an alkyl group, an aryl group, a saturated heterocyclic group, a substituted saturated heterocyclic group, an unsaturated heterocyclic group, a substituted unsaturated heterocyclic group, a pyridine, a substituted pyridine group, or a substituted phenyl group; and R$_4$ and R$_5$ are each independently a methyl group or an ethyl group, or a salt thereof to the subject.

2. The method of claim 1, wherein the nAChR is an α9 nAChR, an α9α10 nAChR, or an α7 nAChR.

3. The method of claim 1, wherein the disease or disorder is a nervous system disorder or a hearing disorder.

4. The method of claim 3, wherein the nervous system disorder is Alzheimer's disease, schizophrenia, depression, attention deficit hyperactivity disorder (ADHD), tobacco addiction, chronic pain, Parkinson's disease, or any combination thereof.

5. The method of claim 3, wherein the hearing disorder is noise-induced hearing loss, vertigo, tinnitus, or any combination thereof.

6. The method of claim 1, wherein the para-substituted 1,1-dialkyl-4-phenylpiperazin-1-ium is selected from the group consisting of the formulae:

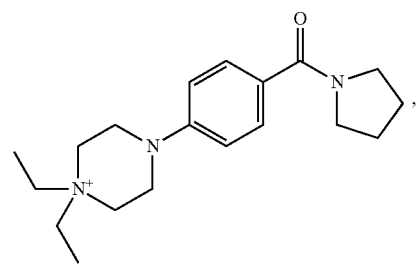
3a

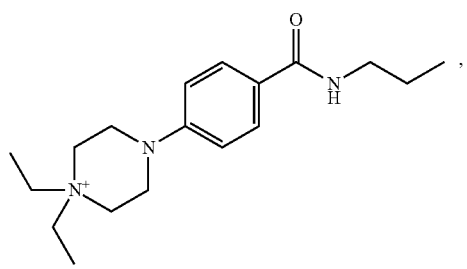
3b

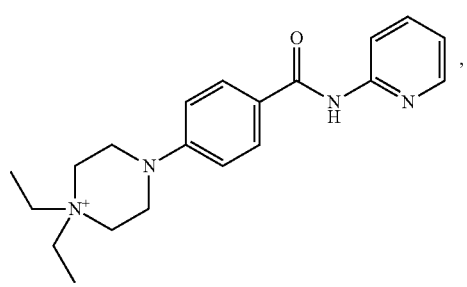
3c

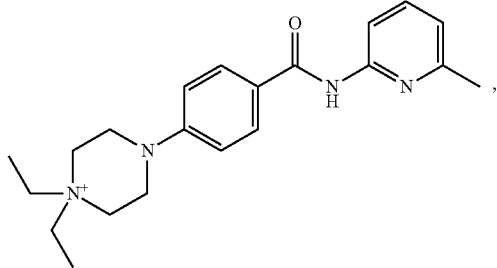
3d

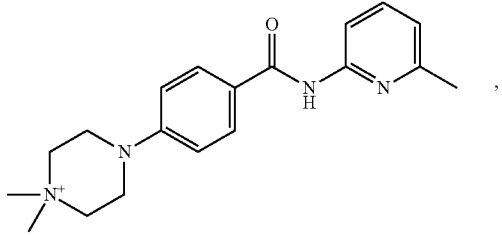
3e

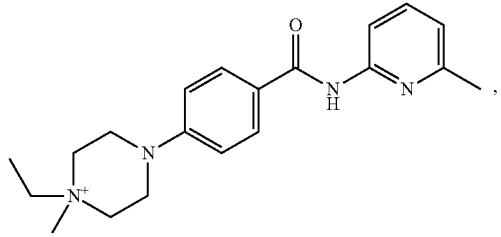
3f

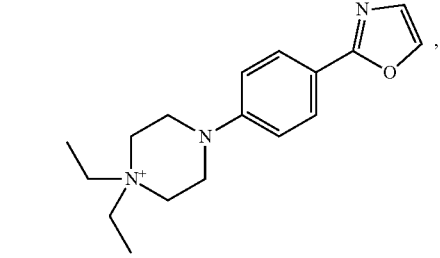
3g

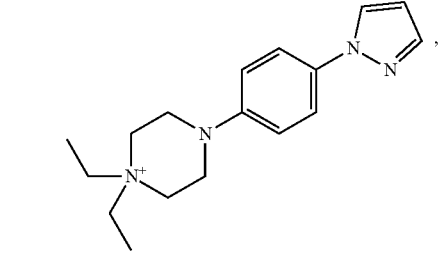
3h

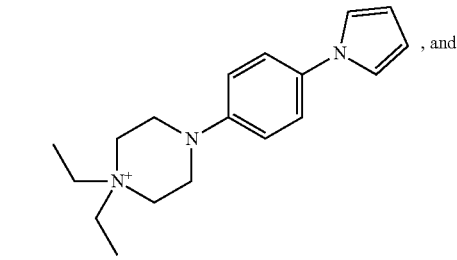
3i
, and

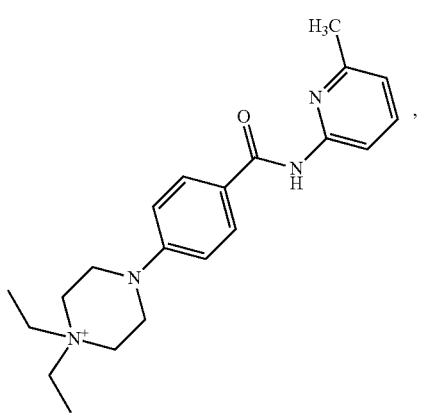

or a salt thereof.

7. The method of claim 1, wherein the salt is an iodide.

8. The method of claim 1, wherein the pharmaceutical composition further comprises at least one pharmaceutically acceptable carrier.

9. The method of claim 1, wherein the pharmaceutically acceptable carrier comprises a diluent, an adjuvants, a vehicle, a non-toxic filler, an encapsulating material, or any combination thereof.

10. The method of claim 2, wherein the nAChR is an α9 nAChR or an α9α10 nAChR and the compound is selected from

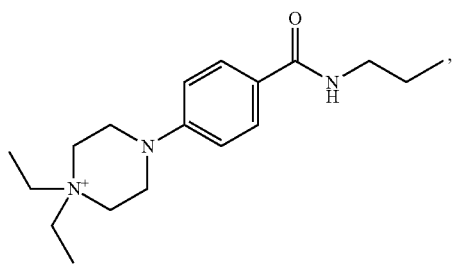

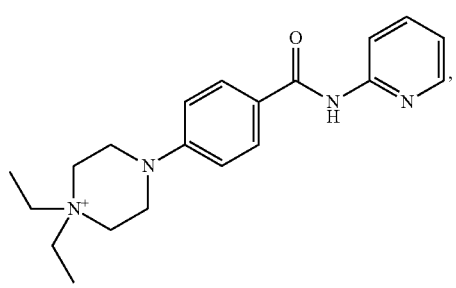

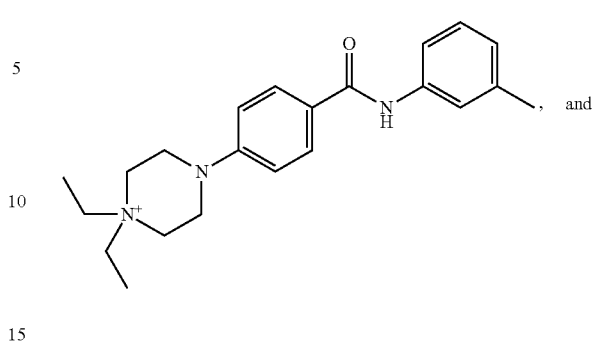

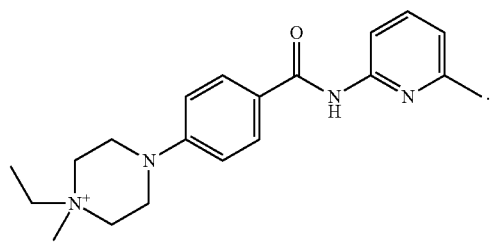

11. The method of claim 2, wherein the nAChR is an α9 nAChR or an α9α10 nAChR and the compound is

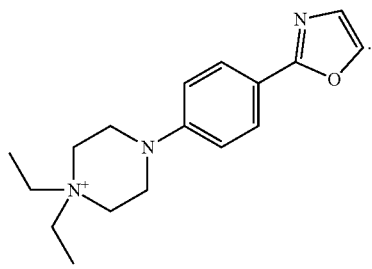

12. The method of claim 2, wherein the compound has an $i_{max}$ of greater than or equal to about 1.13 for the α9 nAChR.

13. The method of claim 2, wherein the compound has an $EC_{50}$ of greater than or equal to about 0.38 for the α9 nAChR.

14. The method of claim 1, wherein the compound or salt thereof is administered orally.

\* \* \* \* \*